(12) United States Patent
Defreitas et al.

(10) Patent No.: US 12,059,279 B2
(45) Date of Patent: Aug. 13, 2024

(54) BREAST COMPRESSION PADDLE UTILIZING FOAM

(71) Applicant: Hologic, Inc., Marlborough, MA (US)

(72) Inventors: Kenneth F. Defreitas, Patterson, NY (US); Alan Rego, Woodbury, CT (US); Richard Gladwin Edwards, Brookfield, CT (US); Zhenxue Jing, Chadds Ford, PA (US); Jay A. Stein, Boston, MA (US); Timothy N. Wells, Manchester, CT (US); Cornell Lee Williams, North East, MD (US)

(73) Assignee: Hologic, Inc., Marlborough, MA (US)

( * ) Notice: Subject to any disclaimer, the term of this patent is extended or adjusted under 35 U.S.C. 154(b) by 0 days.

(21) Appl. No.: 18/362,434

(22) Filed: Jul. 31, 2023

(65) Prior Publication Data
US 2024/0065649 A1   Feb. 29, 2024

Related U.S. Application Data

(60) Continuation of application No. 17/814,369, filed on Jul. 22, 2022, now Pat. No. 11,751,824, which is a
(Continued)

(51) Int. Cl.
*A61B 6/04* (2006.01)
*A61B 6/50* (2024.01)
(Continued)

(52) U.S. Cl.
CPC .......... *A61B 6/0414* (2013.01); *A61B 6/0435* (2013.01); *A61B 6/502* (2013.01); *A61B 6/025* (2013.01); *A61B 6/032* (2013.01)

(58) Field of Classification Search
CPC .................. A61B 6/025; A61B 6/0414; A61B 2018/00333; A61B 6/502; A61B 90/17;
(Continued)

(56) References Cited

U.S. PATENT DOCUMENTS

| 4,744,099 A | 5/1988 | Huettenrauch et al. |
| 5,474,072 A | 12/1995 | Shmulewitz |

(Continued)

FOREIGN PATENT DOCUMENTS

| DE | 102016217599 | 3/2018 |
| JP | 2006-519625 A | 8/2006 |

(Continued)

OTHER PUBLICATIONS

Dibble et al., "Mammography with breast cushions", Women's Health Issues, Elsevier, vol. 15, No. 2, Mar. 1, 2005, 9 pages.
(Continued)

*Primary Examiner* — Don K Wong
(74) *Attorney, Agent, or Firm* — Merchant & Gould P.C.

(57) ABSTRACT

While performing a tomosynthesis procedure, the breast of a patient is compressed between two compression elements to create an imaging condition. Foam is secured to the rigid substrate of a one of the compression elements. The patient's chest wall is aligned with the leading edge surface of the foam. The inner side of the breast is disposed proximate the lateral edge surface of the foam and the outer side of the breast is disposed proximate the outer lateral edge surface of the foam. A mid-plane is disposed between the inner and outer lateral edge surfaces of the foam. An interface connects a leading edge surface of the foam and compressive surfaces. A portion of the leading edge surface which is aligned with the mid-plane is incompletely compressed.

20 Claims, 24 Drawing Sheets

Related U.S. Application Data division of application No. 16/981,934, filed as application No. PCT/US2019/033998 on May 24, 2019, now Pat. No. 11,426,132.

(60) Provisional application No. 62/814,041, filed on Mar. 5, 2019, provisional application No. 62/732,771, filed on Sep. 18, 2018, provisional application No. 62/676,609, filed on May 25, 2018.

(51) Int. Cl.
 *A61B 6/02* (2006.01)
 *A61B 6/03* (2006.01)

(58) Field of Classification Search
 CPC ... A61B 6/0435; A61B 5/4312; A61B 5/0091; A61B 8/403; A61B 5/708; A61B 6/5258; A61B 8/0825
 See application file for complete search history.

(56) References Cited

U.S. PATENT DOCUMENTS

| | | | |
|---|---|---|---|
| 5,506,877 | A | 4/1996 | Niklason et al. |
| 6,577,702 | B1 | 6/2003 | Lebovic |
| 8,401,145 | B1 | 3/2013 | Boutte |
| 8,768,026 | B2 | 7/2014 | Ren et al. |
| 9,883,846 | B2 | 2/2018 | Son |
| 11,751,824 | B2 | 9/2023 | Defreitas et al. |
| 2003/0007597 | A1 | 1/2003 | Higgins |
| 2003/0099325 | A1 | 5/2003 | Galkin |
| 2004/0101095 | A1 | 5/2004 | Jing et al. |
| 2004/0156472 | A1 | 8/2004 | Galkin |
| 2004/0218727 | A1 | 11/2004 | Shoenfeld |
| 2005/0008117 | A1 | 1/2005 | Livingston |
| 2006/0050844 | A1 | 3/2006 | Galkin |
| 2006/0126794 | A1 | 6/2006 | Hermann |
| 2007/0280412 | A1 | 12/2007 | Defreitas et al. |
| 2008/0045833 | A1 | 2/2008 | Defreitas et al. |
| 2009/0135997 | A1 | 5/2009 | DeFreitas et al. |
| 2009/0268865 | A1 | 10/2009 | Ren et al. |
| 2010/0067659 | A1 | 3/2010 | Bush |
| 2010/0179604 | A1 | 7/2010 | Campagna |
| 2012/0114096 | A1 | 5/2012 | Lebovic et al. |
| 2013/0129039 | A1 | 5/2013 | DeFreitas |
| 2014/0177791 | A1 | 6/2014 | Otokuni et al. |
| 2014/0226786 | A1 | 8/2014 | Goossen et al. |
| 2015/0250432 | A1 | 9/2015 | Savagian |
| 2015/0305693 | A1 | 10/2015 | Galambos McLaughlin |
| 2016/0081633 | A1 | 3/2016 | Stango |
| 2016/0183898 | A1 | 6/2016 | Cormican |
| 2016/0206229 | A1 | 7/2016 | Arai et al. |
| 2017/0251991 | A1 | 9/2017 | Wang et al. |
| 2017/0340303 | A1 | 11/2017 | Stango et al. |
| 2018/0125437 | A1* | 5/2018 | Stango ..................... A61B 6/04 |
| 2021/0015435 | A1 | 1/2021 | DeFreitas |
| 2021/0030375 | A1 | 2/2021 | Defreitas et al. |
| 2021/0361246 | A1 | 11/2021 | Defreitas et al. |
| 2023/0022003 | A1 | 1/2023 | Defreitas et al. |
| 2023/0121488 | A1 | 4/2023 | Ren |

FOREIGN PATENT DOCUMENTS

| | | |
|---|---|---|
| JP | 2009-178227 | 8/2009 |
| JP | 2011-206436 | 10/2011 |
| JP | 2011-206438 | 10/2011 |
| JP | 2012-231888 A | 11/2012 |
| JP | 2014-073294 A | 4/2014 |
| JP | 2017-176509 A | 10/2017 |
| TO | 2019/227044 | 11/2019 |
| WO | 2001/066013 | 9/2001 |
| WO | 2007/095330 | 8/2007 |
| WO | 2014/176445 | 10/2014 |
| WO | 2015/018848 | 2/2015 |
| WO | 2016/172294 | 10/2016 |
| WO | 2019/227042 | 11/2019 |
| WO | 2019/227051 | 11/2019 |

OTHER PUBLICATIONS

PCT International Search Report and Written Opinion of the International Searching Authority for International Patent Application No. PCT/US2019/033998 mailed Sep. 24, 2019, 19 pages.

PCT International Preliminary Report on Patentability in International Patent Application No. PCT/US2019/033998 mailed Dec. 10, 2020, 12 pages.

European Communication pursuant to Article 94(3) EPC in Application 19730090.8, mailed Sep. 13, 2023, 5 pages.

Mawdsley, Gordon et al., "Accurate estimation of compressed breast thickness in mammography", Medical physics, 2009, 6 (2), pp. 577-586.

Petru, M., et al "Measurement and Numerical Modeling of Mechanical Properties of Polyurethane Foams", Aspects of Polyurethanes, 2017, pp. 73-109.

\* cited by examiner

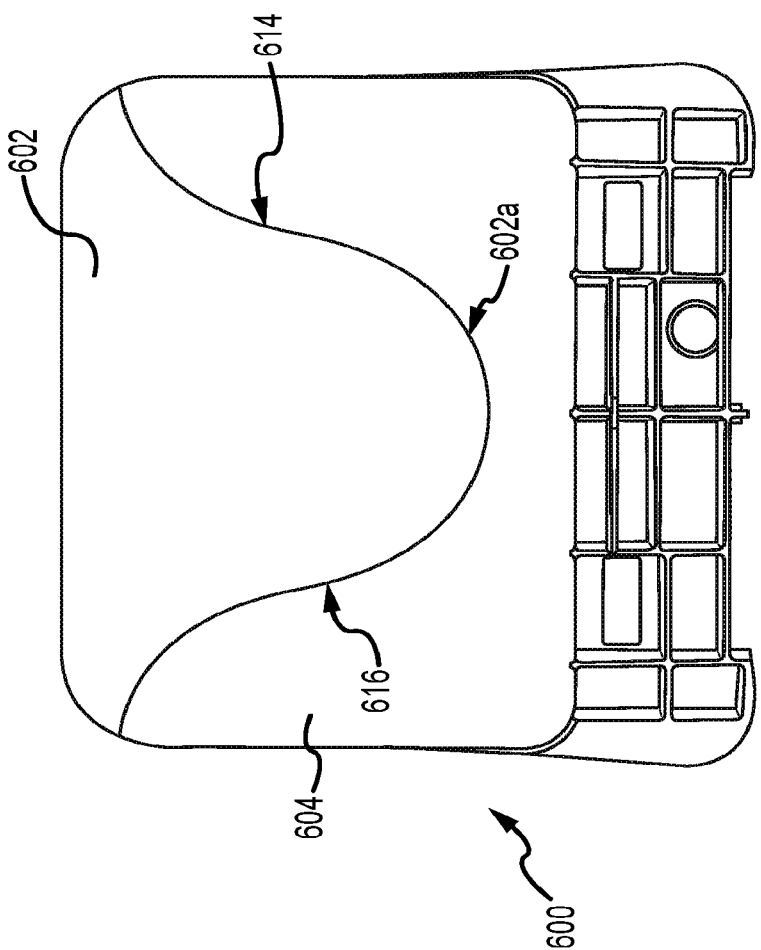

BREAST COMPRESSION PADDLE UTILIZING FOAM

CROSS-REFERENCE TO RELATED APPLICATIONS

This application is a continuation of U.S. patent application Ser. No. 17/824,369, filed Jul. 22, 2022, now U.S. Pat. No. 11,751,824, which is a divisional of U.S. patent application Ser. No. 16/981,934, now U.S. Pat. No. 11,426,132, which is a National Stage Application of PCT/US2019/033998, filed May 24, 2019 which claims the benefit of priority to U.S. Provisional Application No. 62/676,609, filed May 25, 2018, U.S. Provisional Application No. 62/732,771, filed Sep. 18, 2018, and U.S. Provisional Application No. 62/814,041, filed Mar. 5, 2019, which applications are hereby incorporated in their entireties by reference. To the extent appropriate, a claim of priority is made to each of the above disclosed applications.

BACKGROUND

Compression during mammography and tomosynthesis imaging serves a number of purposes. For example, it: (1) makes the breast thinner in the direction of x-ray flux and thereby reduces patient radiation exposure from the level required to image the thicker parts of a breast that are not compressed; (2) makes the breast more uniform in thickness in the direction of x-ray flux and thereby facilitates more uniform exposure at the image plane over the entire breast image; (3) immobilizes the breast during the x-ray exposure and thereby reduces image blurring; and (4) brings breast tissues out from the chest wall into the imaging exposure field and thus allows for more tissue imaging. As the breast is being compressed, typically a technologist manipulates the breast to position it appropriately and counter the tendency that compression has of pushing breast tissue toward the chest wall and out of the image field.

Standard compression methods for mammography and tomosynthesis use a movable, rigid, radiolucent compression paddle. The breast is placed on a breast support platform that typically is flat, and the paddle then compresses the breast, usually while a technologist or other health professional is holding the breast in place. The technologist may also manipulate the breast to ensure proper tissue coverage in the image receptor's field of view.

One known challenge in mammography and breast tomosynthesis is the discomfort the patient may feel when the breast is compressed, which must be done with sufficient force to immobilize the breast and spread out the breast tissues for x-ray imaging. Discomfort may potentially cause the patient to move, which negatively impacts image quality. Discomfort may also potentially dissuade patients from getting screened for breast cancer. Another known challenge is to ensure that the imaged field includes the desired amount of breast tissue.

SUMMARY

In one aspect, the technology relates to a method of compressing a breast of a patient for a tomosynthesis imaging procedure, the method including: providing a first compression element has a rigid substrate and a foam secured to the rigid substrate, wherein the foam includes an inner lateral edge surface, an outer lateral edge surface, a mid-plane disposed between the inner lateral edge surface and the outer lateral edge surface, a leading edge surface, a compressive surface, and an interface connecting the leading edge surface and the compressive surface; disposing the breast proximate a second compression element disposed facing the compressive surface, wherein a chest wall of the patient is substantially aligned with the leading edge surface, and wherein an inner side of the breast is disposed proximate the inner lateral edge surface and an outer side of the breast is disposed proximate the outer lateral edge surface; compressing the breast between the first compression element and the second compression element to an imaging condition, wherein in the imaging condition, a portion of the leading surface aligned with the mid-plane is compressed to an incompletely compressed condition; and performing the tomosynthesis imaging procedure. In an example, when in the imaging condition, the interface defines a first curve adjacent an outer side of the mid-plane and a second curve adjacent an inner side of mid-plane. In another example, when in the imaging condition, a straight portion of the interface is substantially parallel to the second compression element. In yet another example, the method further includes removing a removable portion of the foam prior to disposing the breast on the second compression element. In still another example, the method further includes inserting the removable portion of the foam prior to compressing the breast.

In another example of the above aspect, the removable portion includes a plurality of removable portions. In an example, the method further includes processing an output from the imaging procedure so as to adjust a visibility of an artifact formed by the removable portion. In another example, at least one of the inner lateral edge surface and the outer lateral edge surface is curved. In yet another example, the first compressive element is a breast platform and the second compressive element is a compression paddle.

In another aspect, the technology relates to a breast compression paddle having: a bracket for removably securing the breast compression paddle to an imaging system; a rigid substrate secured to the bracket; a foam secured to the rigid substrate; and an accessory having at least one of (a) a measuring device configured to move relative to the rigid substrate and (b) a removable portion of foam. In an example, the accessory includes the measuring device, wherein the measuring device has at least one rigid pin secured proximate the foam, wherein a vertical compression of the foam moves the rigid pin. In another example, the rigid pin is disposed substantially within the foam when the foam is in an uncompressed state. In yet another example, a bottom surface of the rigid pin is substantially level with a compressive surface of the foam. In still another example, a portion of the rigid pin includes an electronically readable media.

In another example of the above aspect, the accessory includes the removable portion of foam. In an example, the removable portion has a plurality of removable portions. In another example, the removable portion extends across both a width and a length of the foam. In yet another example, the removable portion is only partially surrounded by a non-removable portion of foam. In still another example, the removable portion is surrounded by a non-removable portion of foam.

In another aspect, the technology relates to a method of compressing a breast for an imaging procedure, the method includes: providing a compression paddle having a main rigid substrate, a main foam secured to the main rigid substrate, and a subsidiary foam movably secured relative to the main foam; moving the subsidiary foam into a non-contacting position; positioning the breast on a support platform; contacting a portion of the breast with the main foam, while the subsidiary foam remains in the non-contacting position; moving the subsidiary foam relative to the main foam and into a contacting position; and compressing the breast with both the main foam and the subsidiary foam. In an example, the method further includes at least partially compressing the portion of the breast with the main foam while the subsidiary foam remains in the non-contacting position. In another example, moving the subsidiary foam into the contacting position includes positioning the subsidiary foam proximate the main rigid substrate. In yet another example, moving the subsidiary foam into the contacting position includes positioning the subsidiary foam adjacent the main foam. In still another example, moving the subsidiary foam into the contacting position includes securing the subsidiary foam against movement.

In another aspect, the technology relates to a method of calculating a thickness of a compressed breast, the method including: at least partially compressing a breast between a support platform and a compression paddle, wherein the compression paddle includes a compressive foam material in contact with the breast; determining a separation distance between a surface of the compression paddle and a surface of the support platform; determining an offset distance of the breast from the compression paddle, wherein the offset distance corresponds to a compressed thickness of the compressive foam material; and calculating a breast thickness based at least in part on the separation distance and the offset distance. In an example, the offset distance is determined by reading automatically a compression detector. In another example, the method further includes calculating an x-ray exposure technique based at least in part on the breast thickness.

In another aspect, the technology relates to a method of determining a radiation dose for a compressed breast, the method including: at least partially compressing a breast between a support platform and a compression paddle, wherein the compression paddle has a compressive foam material in contact with the breast; acquiring a set of tomosynthesis images of the compressed breast; determining a thickness of the compressed breast based at least in part on the tomosynthesis images; determining a density of the compressed breast based at least in part on the tomosynthesis images; and calculating a breast dose based at least in part on the determined thickness and density.

In another aspect, the technology relates to a breast compression paddle having: a bracket for removably securing the breast compression paddle to an imaging system; and a foam pad secured relative to the bracket, wherein the foam pad includes a first foam of a first density and a second foam of a second density. In an example, the foam pad includes a compression surface configured to contact a breast during compression, wherein the compression surface is substantially parallel to the rigid substrate, wherein the first foam contacts the second foam at an abutment, and wherein the abutment is disposed at an angle to the compression surface. In another example, the first foam forms at least a portion of the compression surface. In yet another example, the first foam and the second foam form at least a portion of the compression surface. In still another example, the first foam and the second foam define discrete volumes within the foam pad.

In another example of the above aspect, the first foam has a density greater than a density of the second foam. In an example, the breast compression paddle further includes a substrate securing the bracket to the foam pad. In an example, the foam pad has a compression surface configured to contact a breast during compression, wherein the compression surface is substantially parallel to the rigid substrate, wherein the first foam contacts the second foam at an abutment, and wherein the abutment is disposed substantially parallel to the compression surface.

In another aspect, the technology relates to a breast compression paddle for use in an imaging system, the breast compression paddle having: a pair of rigid side walls; a rigid base spanning the pair of rigid sidewalls; a rigid front wall connected to the rigid base and each of the pair of side walls; a tensioner extending from at least one of the pair of side walls; a thin flexible material at least partially disposed about the compression paddle, wherein the tensioning element is configured to maintain a tension of the thin flexible material about the compression paddle; and a foam profile secured to the rigid base, wherein the foam profile is disposed between the rigid base and the thin flexible material. In an example, the foam profile is at least partially cylindrical. In another example, the foam profile includes a plurality of foam profiles. In yet another example, a portion of the foam profile is curved. In still another example, a first foam profile of the plurality of foam profiles is disposed proximate a first of the pair of rigid side walls, and wherein a second foam profile of the plurality of foam profiles is disposed proximate a second of the pair of rigid side walls.

In another example of the above aspect, the tensioner is integral with at least one of the pair of rigid side walls. In an example, the thin flexible material is shaped like a bag. In another example, the thin flexible material contacts the pair of rigid side walls and the rigid front wall.

In another aspect, the technology relates to a breast compression paddle for use in an imaging system, the breast compression paddle having: a pair of side walls each having a resilient extension; a rigid base connecting the pair of side walls; a pair of foam profiles secured to the rigid base and disposed proximate each of the pair of side walls; and a thin flexible material at least partially disposed about the pair of side walls and the pair of foam profiles. In an example, the pair of foam profiles are connected to the rigid base with an adhesive. In another example, an application of a force to the thin flexible material at least partially deflects the thin flexible material and at least partially compresses the pair of foam profiles. In yet another example, an application of a force to the thin flexible material at least partially deflects the resilient extensions. In still another example, an uppermost compressive surface of the rigid base is disposed above an uppermost extent of each of the pair of foam profiles.

In another example of the above aspect, each of the pair of foam profiles is shaped similar to a half-cylinder. In an example, the thin flexible material has a bag-like structure. In another example, the breast compression paddle further includes a front wall connected to the rigid base. In yet another example, the front wall separated from the pair of side walls by a plurality of gaps. In still another example, the breast compression paddle further includes a bracket connected to the rigid base, the bracket configured to connect the breast compression paddle to an imaging system. In an example, the bracket is separated from the pair of side walls by a plurality of gaps.

In another aspect, the technology relates to a breast imaging system having the breast compression paddle.

BRIEF DESCRIPTION OF THE DRAWINGS

FIG. 8 is a top view of a compression paddle having a foam compressive element in accordance with another example.

DETAILED DESCRIPTION

Figure 1A:
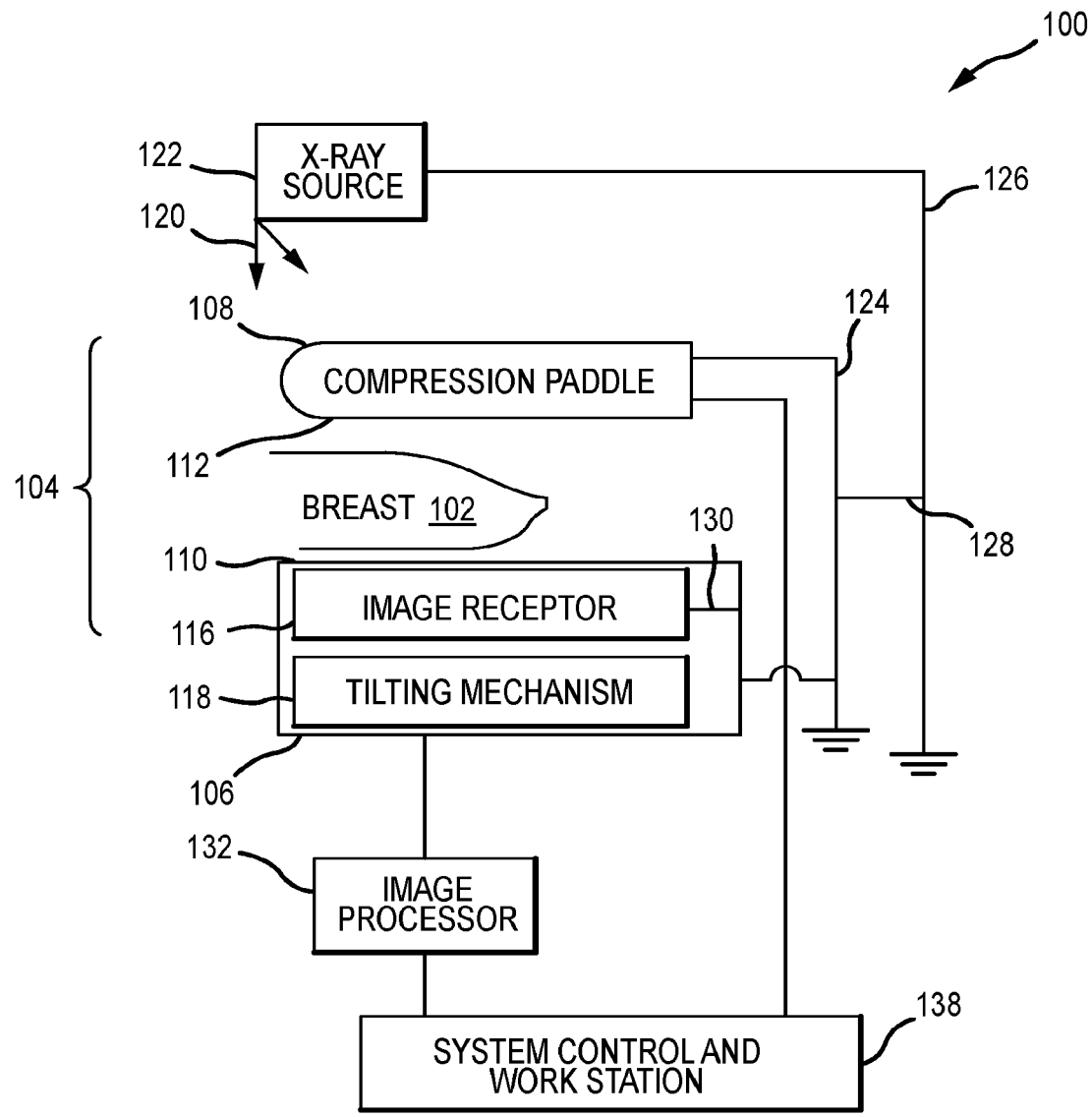
FIG. 1A is a schematic view of an exemplary imaging system.
Figure 1B:
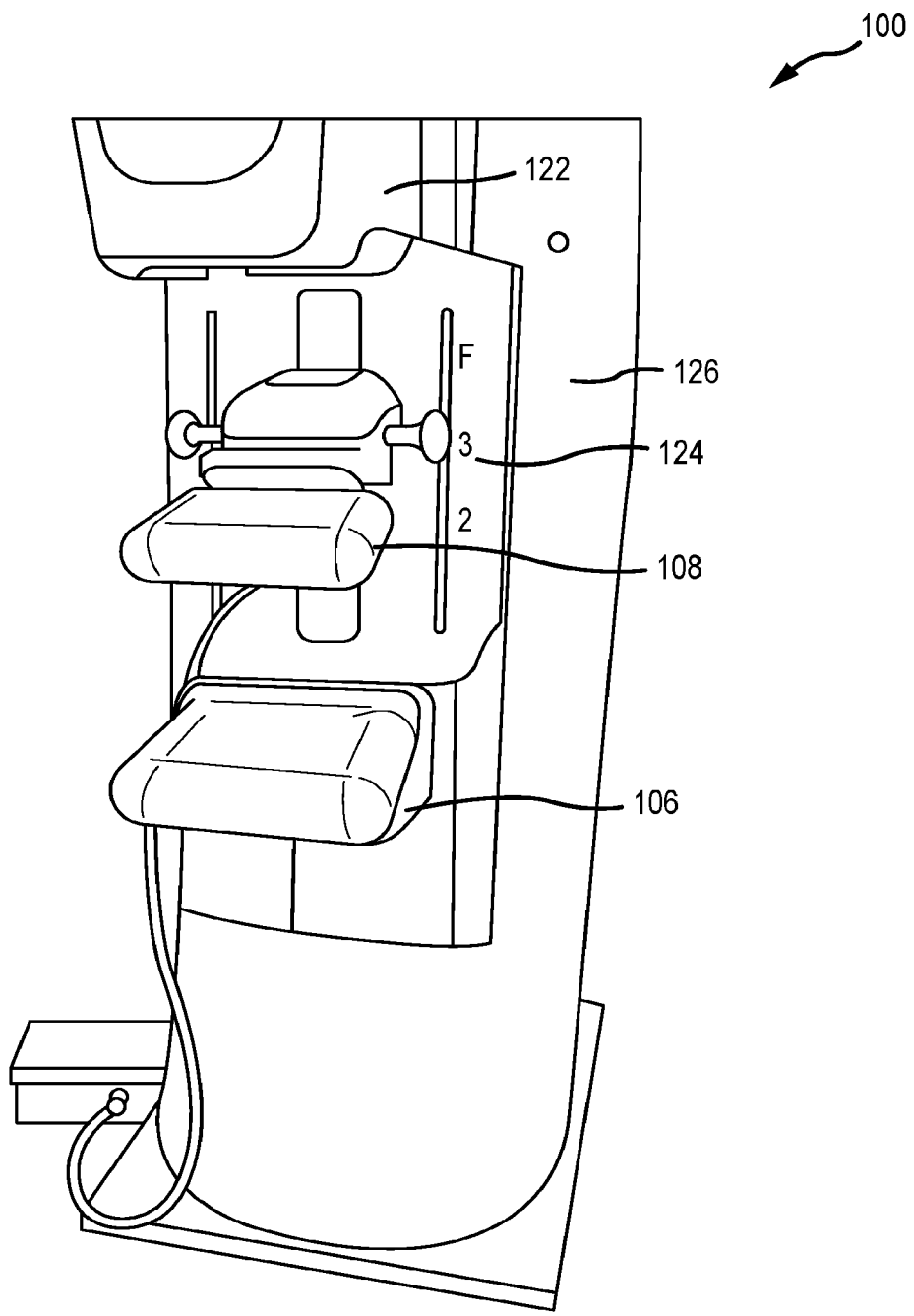
FIG. 1B is a perspective view of the imaging system of FIG. 1A.

FIG. 1A is a schematic view of an exemplary imaging system 100. FIG. 1B is a perspective view of the imaging system 100. Referring concurrently to FIGS. 1A and 1B, the imaging system 100 immobilizes a patient's breast 102 for x-ray imaging (either or both of mammography and tomosynthesis) via a breast compression immobilizer unit 104 that includes a static breast support platform 106 and a moveable compression paddle 108. The breast support platform 106 and the compression paddle 108 each have a compression surface 110 and 112, respectively, that move towards each other to compress and immobilize the breast 102. In known systems, the compression surface 110, 112 is exposed so as to directly contact the breast 102. The platform 106 also houses an image receptor 116 and, optionally, a tilting mechanism 118, and optionally an anti-scatter grid. The immobilizer unit 104 is in a path of an imaging beam 120 emanating from x-ray source 122, such that the beam 120 impinges on the image receptor 116.

The immobilizer unit 104 is supported on a first support arm 124 and the x-ray source 122 is supported on a second support arm 126. For mammography, support arms 124 and 126 can rotate as a unit about an axis 128 between different imaging orientations such as CC and MLO, so that the system 100 can take a mammogram projection image at each orientation. In operation, the image receptor 116 remains in place relative to the platform 106 while an image is taken. The immobilizer unit 104 releases the breast 102 for movement of arms 124, 126 to a different imaging orientation. For tomosynthesis, the support arm 124 stays in place, with the breast 102 immobilized and remaining in place, while at least the second support arm 126 rotates the x-ray source 122 relative to the immobilizer unit 104 and the compressed breast 102 about the axis 128. The system 100 takes plural tomosynthesis projection images of the breast 102 at respective angles of the beam 120 relative to the breast 102.

Concurrently and optionally, the image receptor 116 may be tilted relative to the breast support platform 106 and in sync with the rotation of the second support arm 126. The tilting can be through the same angle as the rotation of the x-ray source 122, but may also be through a different angle selected such that the beam 120 remains substantially in the same position on the image receptor 116 for each of the plural images. The tilting can be about an axis 130, which can but need not be in the image plane of the image receptor 116. The tilting mechanism 118 that is coupled to the image receptor 116 can drive the image receptor 116 in a tilting motion. For tomosynthesis imaging and/or CT imaging, the breast support platform 106 can be horizontal or can be at an angle to the horizontal, e.g., at an orientation similar to that for conventional MLO imaging in mammography. The system 100 can be solely a mammography system, a CT system, or solely a tomosynthesis system, or a "combo" system that can perform multiple forms of imaging. An example of such a combo system has been offered by the assignee hereof under the trade name Selenia Dimensions.

When the system is operated, the image receptor 116 produces imaging information in response to illumination by the imaging beam 120, and supplies it to an image processor 132 for processing and generating breast x-ray images. A system control and work station unit 138 including software controls the operation of the system and interacts with the operator to receive commands and deliver information including processed-ray images.

One challenge with the imaging system 100 is how to immobilize and compress the breast 102 for the desired or required imaging. A health professional, typically an x-ray technologist, generally adjusts the breast 102 within the immobilizer unit 104 while pulling tissue towards imaging area and moving the compression paddle 108 toward the breast support platform 106 to immobilize the breast 102 and keep it in place, with as much of the breast tissue as practicable being between the compression surfaces 110, 112.

The present technology relates to a breast compression system having a foam compressive element and/or other components as described below for use in a breast imaging system. During imaging of a breast, it is often desirable to immobilize the breast through compression. For instance, by compressing the breast, the breast can be made thinner, thus requiring a lower dose of radiation. Further, by immobilizing the breast, image blurring from movement of the breast during imaging is reduced. Other benefits may also be realized by compressing the breast.

The paddle may also cause discomfort to the patient whose breast is being compressed. One reason for discomfort that the patient may feel is that the compression force is non-uniformly distributed throughout the breast. It is often concentrated at the thickest portion of the breast, usually near the chest wall, at or near the lower front edge of the compression paddle and the upper front corner of the breast platform. The anterior portion of the breast, such as near the nipple, may receive less compressive force, or no compressive force. The paddle may not even contact this portion of the breast. (The terms front, lower, and upper pertain to using a craniocaudal (CC) imaging orientation, with the patient facing the front of the imaging system, although it should be understood that other imaging orientations, including mediolateral oblique (MLO), are used with the same equipment.)

To improve these issues, the compression systems described herein include a foam compressive element that is positioned over a compression surface and contacts the breast during compression. Although described generally in the context of foam disposed on a compression paddle, foam may additionally or alternatively be disposed on a breast support platform. The foam compresses as pressure increases and is generally more comfortable than hard plastic paddles. Other features may be utilized to improve technologist visibility of the breast during compressive procedures, as well as to determine the amount of foam compression. Appropriate foam materials include super soft urethane foams, such as fire-retardant upholstery foams, that display advantageous performance characteristics. Such materials may be manufactured so as to meet the requirements of ASTM D 3574. Foams having the performance characteristics displayed in Table 1 below have displayed advantageous properties, although other foams having different performance characteristics may also be utilized.

TABLE 1

Super Soft Foam Performance Data

| Property | Test Method | Values |
| --- | --- | --- |
| Density (LB/Cubic Ft.) | ASTM D 3574 | 1.2 |
| 25% ILD (LB) | ASTM D 3574 | 12 |
| Support Factor (65%/25% Min.) | ASTM D 3574 | 1.9 |
| Air Flow (CFM) Min. | ASTM D 3574 | 3 |
| Tensile (PSI) Min. | ASTM D 3574 | 10 |
| Elongation (%) Min. | ASTM D 3574 | 200 |
| Tear (PPI) Min. | ASTM D 3574 | 1.1 |
| Resiliency (%) Min. | ASTM D 3574 | 40 |

Additionally, a foam compressive element may be manufactured of two or more foams having different properties (e.g. densities) so as to change the compression of the breast.

Further testing has been performed to identify desirable foams that may be utilized as thick foam compressive elements. For example, a noise power spectrum study has been performed. In the study, a 2 inch piece of foam was compressed to various thicknesses on a Selenia Dimensions system available from the assignee hereof. Detector signals were all matched in the study and it was determined that noise changes were all due to the utilization of a foam compressive element. It was further determined that compression helps to reduce the noise generated by the foam, expect when compressed to below 2 cm thickness where further noise reduction becomes less significant. As the magnitude was increased, a spectrum shape change was also observed. Further, the noise from the foam was both high and low frequency, although low frequency noise was more enhanced in the foam images. Further results are depicted in Tables 2 and 3, below.

TABLE 2

Magnitude Study

| | sig | nos | nos ratio |
| --- | --- | --- | --- |
| no foam | 471 | 6.31 | 1.000 |
| foam at 0 cm | 469 | 7.11 | 1.127 |
| foam at 10 cm | 470 | 6.88 | 1.090 |
| foam at 20 cm | 471 | 6.70 | 1.062 |
| foam at 34 cm | 472 | 6.54 | 1.036 |

TABLE 3

Compression Study

| | sig | nos | nos ratio |
| --- | --- | --- | --- |
| no foam | 471 | 6.31 | 1.000 |
| foam of 5.2 cm | 472 | 7.09 | 1.123 |
| foam of 2 cm | 472 | 6.86 | 1.087 |
| foam of 1 cm | 472 | 6.81 | 1.080 |
| foam of 0.6 cm | 472 | 6.79 | 1.076 |

The foam may be secured to a hard plastic compression paddle substrate with a radiotranslucent adhesive, or may be mechanically secured thereto, for example, with hooks, straps, or other securement structures. The foam at least partially conforms in shape to the breast as the paddle is lowered and the foam compresses thus stabilizing the breast for imaging, without requiring the compression pressure typical in breast imaging systems. The foam can also be placed underneath the breast (e.g., secured to the breast support platform). Additionally, the foam may be placed on the portions of the compression paddle and breast platform that face the chest wall. As the compression paddle is lowered, the foam compresses and takes on a curved shaped that approximates the shape of the breast. However, unlike hard plastic compression paddles, compression forces need not be so high as to completely flatten the breast. Rather, the foams described herein are utilized to stabilize the breast, not necessarily to effectuate full compression, which is usually performed by flat rigid compression paddles (or by breast compression elements that have a very thin layer of foam disposed thereon. In a traditional mammogram system, since the breast is not flat, the appearance of the breast would differ (depending on the level of compression of the particular volume of interest), although this appearance may be corrected by image processing algorithms. For imaging systems such as tomosynthesis, however, the foam only appears in slices outside of the boundaries of the breast. For slices inside the breast, the structures blur out and are not visible. As such, the paddles utilizing foams described herein may be used for both mammography and tomosynthesis imaging, although some post-imaging processing may be required to realize all advantages thereof.

The proposed technology contemplates a number of features. For example, the foam may be rectangular in shape and have outer dimensions sized to match the image receptor size. For ease of manufacturing, the foam may be uniformly shaped, such as a rectangular prism. Other alternative examples may include a non-uniform shape, such as greater thickness at breast contacting portion or greater thickness at edges. Greater thickness at the areas of the foam proximate the edges of the breast may help the foam further conform to and stabilize the breast. In examples, the foam may include a width between lateral edge surfaces thereof, and a length between a leading edge surface and a trailing edge surface. In one example, the dimensions of the foam may be about 30 cm wide×24 cm long. In examples, the foam may be about 3 inches thick, about 2 inches thick, or about 1 inch thick. The desired thickness may be dependent on a number of factors including breast size, breast density, compression paddle size, and so on. As noted elsewhere herein, the foam may include a mounting mechanism for connection to a compression paddle or a breast platform. In examples, the mounting mechanism may instead be a permanent or semi-permanent adhesive.

A cover may be disposed on the surfaces of the foam that contact the breast. The cover prevents the foam from absorbing sweat or other bodily fluids which may cause damage to the foam or unsanitary conditions. The cover may be antimicrobial, cleanable, and fluid-resistant; it is also desirable that the cover is sufficiently pliable so as not to adversely affect the deformation of the foam during compression. The cover should also be resistant to cleaning chemicals that may be utilized to sanitize the cover between patients. Disposable covers are also contemplated. Such covers may be easier to use; technologists may simply remove and dispose of the cover between patients. By applying the cover prior to a new procedure, the technologist may give the patient a further impression of being in a sanitary facility. Disposable covers may be stored in a dispenser within the procedure room or on the imaging equipment. In another example, the cover may be formed of a continuous roll of appropriate material mounted on the compression paddle (e.g., proximate a bracket thereof), but removed from the imaging area. A new clean portion of cover may be unrolled and placed into contact with the foam for each new patient.

Since a thick foam compressive element may increase difficulty in properly positioning the breast prior to compression, the technologies described herein incorporate further features that help increase visibility of and access to the breast. These include locating thick foam compressive elements or discrete portions of the compressive paddle, utilizing removable portions of foam, and/or locating thick foam compressive elements on locations of the paddle that enable easier access to the breast.

Figure 2A:
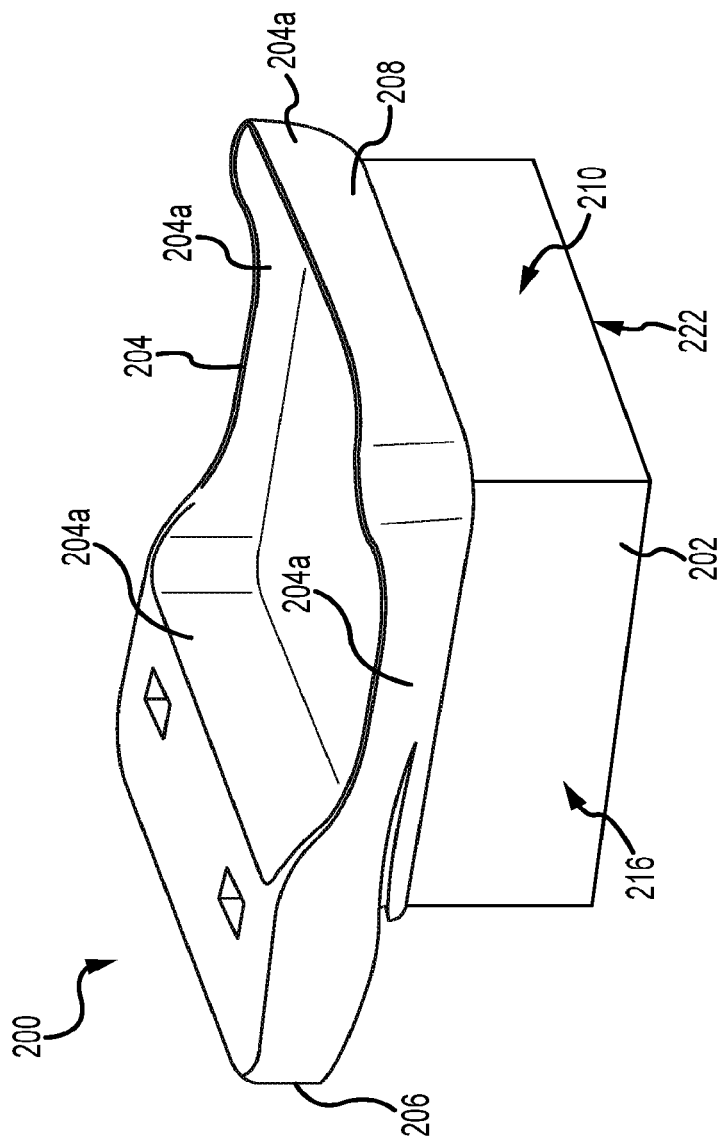
FIG. 2A-2C are various views of a breast compression paddle having a foam compressive element.
Figure 2B:
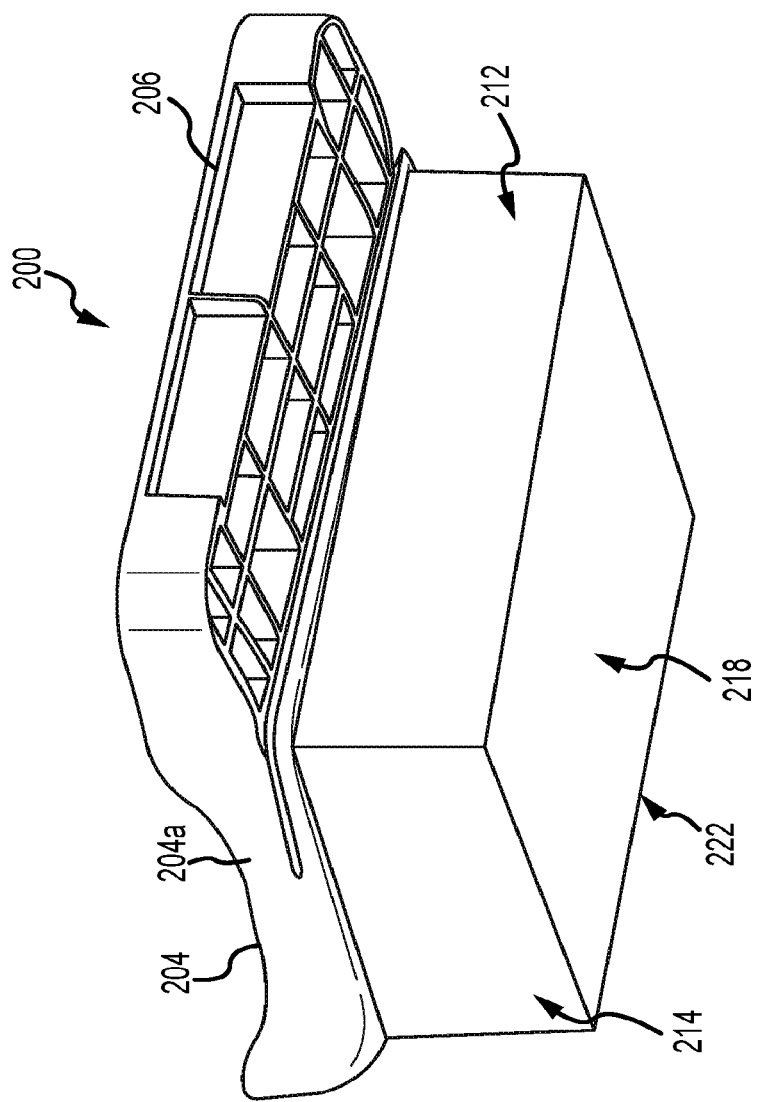
Figure 2C:
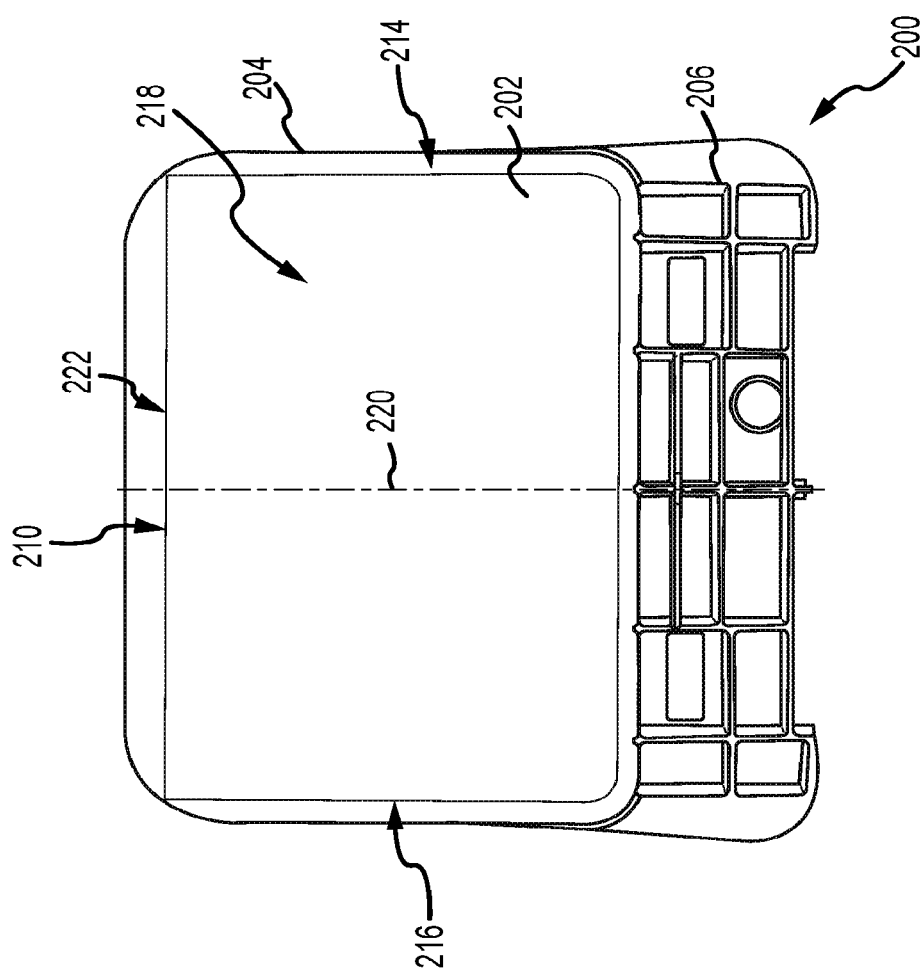

FIGS. 2A-2C are various views of a breast compression paddle 200 having a foam compressive element 202 secured to a rigid substrate 204. FIGS. 2A-2C are described concurrently. The paddle 200 includes a bracket portion 206, generally integral with the substrate 204 for connecting the paddle to compression arm of an imaging system. The paddle 200 also includes a leading face 208, opposite the bracket portion 206, which is disposed proximate a chest wall of a patient during compression and imaging procedures. In examples, the substrate may be rigid. As used herein, the term "rigid" does not imply that the substrate 204 is free from bending during compression of a breast, rather that the substrate 204 displays greater resistance to bending or deformation than the foam compressive element 202 secured to a bottom of the substrate 204. Raised walls 204a provide additional rigidity.

The foam compressive element 202 may be secured to a bottom surface of the substrate 204 with a chemical adhesive. In other example, an upper surface of the compressive element may be a rigid plastic or other material to which the foam compressive element 202 is secured. A plurality of bolts, hooks, or other mechanical fasteners (not shown) may be used to connect this rigid plastic to the rigid substrate 204 of the paddle 200. If such mechanical fasteners are used, it may be desirable to dispose said fasteners away from areas of the foam compressive material 202 that are expected to compress against a breast, so as to avoid pressure points and resulting discomfort associated therewith, as well as to prevent artifacts from appearing in any resulting x-ray images.

The foam compressive element 202 includes a number of edge surfaces. A leading edge surface 210 is disposed proximate the leading face 208 of the substrate 204 so as to be disposed proximate the chest wall of a patient during compression and imaging procedures. A trailing edge surface 212 is disposed opposite the leading edge surface 210, proximate the bracket portion 206. Lateral edge surfaces 214, 216 are also depicted. In general, these lateral edge surfaces 214, 216 may be depicted as inner or outer lateral edge surfaces, consistent with terminology typically used to describe inner and outer sides of the breast. Of course, a person of skill in the art will recognize that the same compression paddle 200 may be used to compress either breast, one at a time, which would effectively change the application of the terms "inner" and "outer" to the lateral edge surfaces of the foam compressive material 202. Further, a mid-plane 220 is disposed between the lateral edge surfaces 214, 216, at an approximate midpoint thereof. The mid-plane 220 is disposed substantially orthogonal to a compressive surface 218 that is disposed on an underside of the foam compressive material 202. Portions of the compressive surface 218 will contact the breast during compression. In another example, the foam compressive material 202 may be covered with a biocompatible cover, which may protect the foam compressive material 202 from absorbing bodily fluids. In examples, the may be disposable or cleanable. To improve the patient experience, the cover may be manufactured of a soft material where it contacts the patient. To prevent fluid transfer into the foam compressive material 202, an opposite plastic side may contact the foam compressive material 202. An interface 222 is located where the compressive surface 218 meets the leading edge surface 210. The shape of the interface 222 during compression aids in defining the foam compressive material 202 and the function thereof.

Figure 2D:
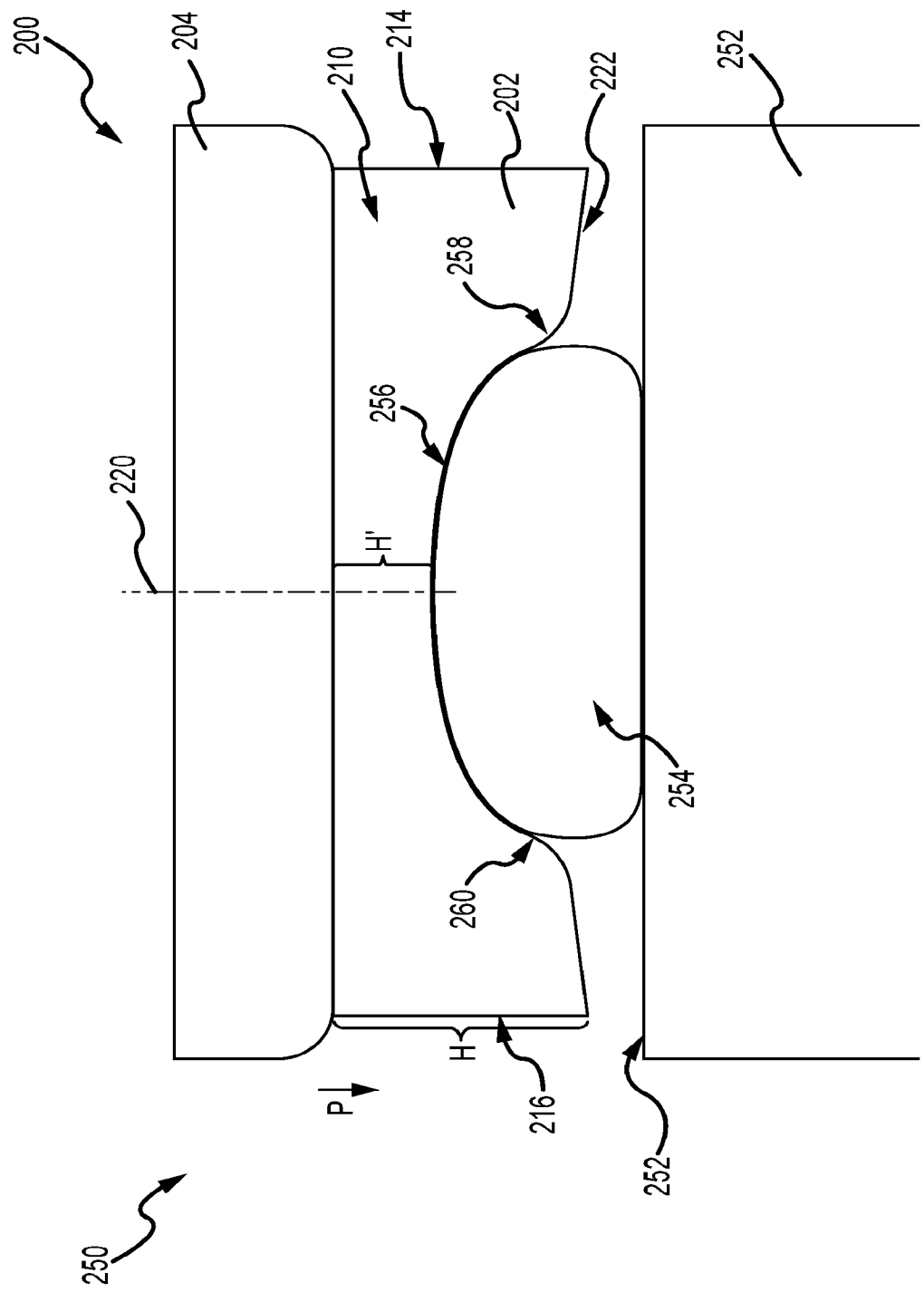
FIG. 2D is a front view of the breast compression paddle of FIGS. 2A-2C compressing a breast.

FIG. 2D is a front view of a compression system 250 for an imaging system. The compression system 250 includes a first compression element in the form of a compression paddle 200 having a rigid substrate 204 and a foam compressive element 202 secured thereto. A second compression element, in this case a breast support platform 252 is also depicted. A breast 254 resting on an upper surface 256 of the breast support platform 252 is also depicted. During use, the breast 254 is compressed by application of a force F by the compression paddle 200. The foam compressive material 202 deforms and conforms to the contours of the breast 254 as compression increases. As such, as the force F is increased, compression of both the breast 254 and foam compressive material 202 occurs. This compression may be defined by the percentage of compression of the foam compressive material 202 proximate the mid-plane 220 at the leading edge surface 210, when the breast 254 is substantially centered along the mid-plane 220. In other examples, the contours of the interface 222 may define the compression of the foam compressive material 202.

As described above, the foam compressive material 202 has an uncompressed height H of the front edge surface 210. In examples, the uncompressed height H may be about one inch to about two inches. In another example, the uncompressed height H may be about two inches to about three inches. In another example, the uncompressed height H may be in excess of about three inches. It has been determined through testing that an uncompressed height H of about three inches is sufficient for compression of a significant number of breast sizes, from small to large. Prior to a tomosynthesis imaging procedure, the breast 254 may be compressed to an imaging condition, which in one example, is a condition to sufficiently stabilize the breast and compress the breast somewhat. Unlike in prior systems where compression with a hard compression paddle results in significant flattening of the breast, the imaging condition to which the breast is compressed need only be to a thickness where the resultant tomosynthesis images are a manageable number. Such a manageable number may be a diagnostically significant number, such that the resulting breast image slices may provide sufficient distinction between slices, but without having such a large number of images, which would necessitate significantly more review time by a clinician.

In examples, this imaging condition of the breast 254 is reached prior to complete compression of the foam compressive material 202 at the front edge surface 210. FIG. 2D depicts compression of the foam compressive material to a maximum amount required for the breast 254 to be in the imaging condition. For illustrative purposes, FIG. 2D depicts the breast 254 centered on the mid-plane 220 of the foam compressive material 202. Thus, a portion of the foam compressive element 202 at this position is not completely compressed and is depicted in FIG. 2D as incompletely compressed height H'. This incompletely compressed height H' is the portion of the foam compressive material 202, measured at the leading edge surface 210 that, while the most compressed portion of the foam compressive material 202, may still be compressed further if further force was applied to the breast 254. In examples, the imaging condition of the breast may be reached when only a portion of the foam compressive material 202 reaches a completely compressed height H'.

The shape of the interface 222 may define the compression of the foam compressive material 202. Unlike prior art thin foam pads, where an interface between the compressive surface and a leading edge surface is pressed substantially flat along the entire length of the breast, the foam compressive material 202 of the present technology maintains a curved shaped along much of the entire breast 254. The interface 222, for example, defines a generally smooth curvature 256 from a first contact point 258 proximate an inner side of the breast 254 to a second contact point 260 proximate an outer side of the breast 254. Prior art thin foam pads, however, are almost flat from a first contact point to a second contact point.

Unlike prior art foam pads that are thin cushions, the foam compressive materials 202 described herein are of a thickness that a significant portion of material between the breast and the supporting rigid substrate need not be completely compressed prior to the breast reaching the imaging condition. "Completely compressed," as used in this context, contemplates a condition where a portion of the foam compressive material has been compressed such that no further compression of the foam is possible with the imaging system on which the breast is stabilized and with which it is imaged. Indeed, in conditions where complete compression of a thin foam is attained, further application of force often results in significant discomfort to the patient, as the foam material has been so completely compressed that it no longer provides any noticeable level of cushioning. Indeed, when foam is completely compressed, the compression sensation is more akin to that of a rigid paddle that utilizes no foam whatsoever. Depending on factors such as size and density of the breast, the portions of the thick foams that compress completely are limited as compared to thinner foam materials, which may reach a completely compressed condition along substantially the area of contact with the breast. In examples of the present technology, complete foam compression may occur only proximate the chest wall and from a predetermined distance away from the chest wall, as opposed to along substantially the entire area of the compressed breast, as common with thin foam applications.

Figure 3A:
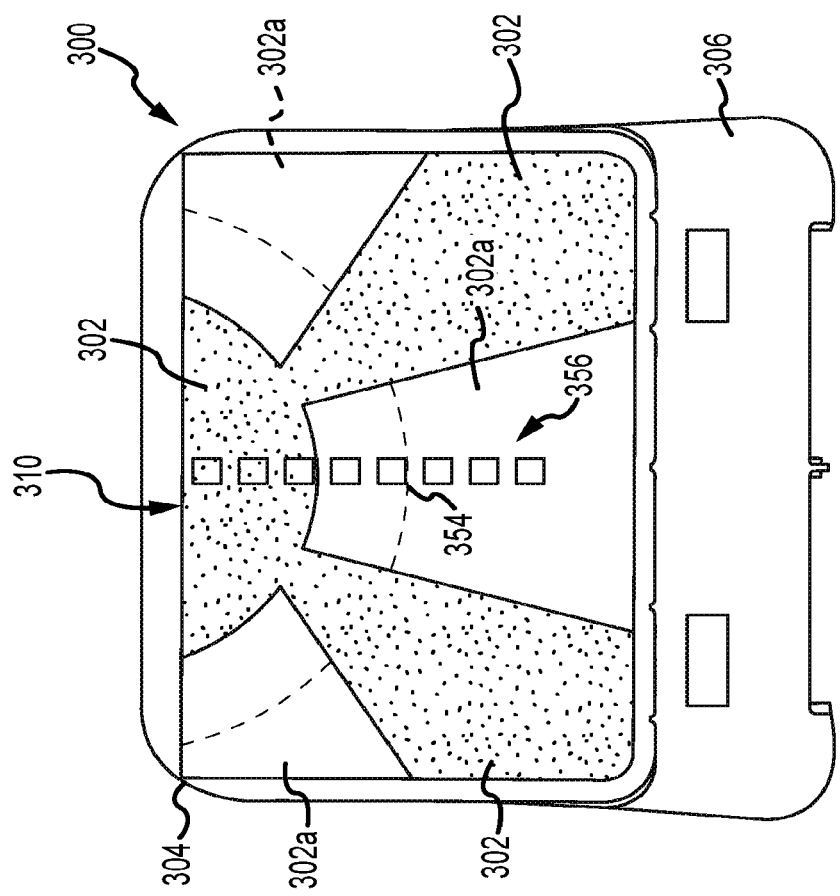
FIG. 3A is a top view of a compression paddle having a removable portion of a foam compressive element in accordance with an example.

FIG. 3A is a top view of a compression paddle 300 having a removable portion 302a of a foam compressive material 302 in accordance with an example. While a foam compressive material 302 has particular advantages as described above and elsewhere herein, use thereof can make positioning of a breast somewhat difficult for a technologist, since the foam compressive material 302 is not transparent. In that regard, the proposed technology contemplates a foam compressive material 302 having one or more subsidiary removable portions 302a. These subsidiary portions 302a may be removed prior to significant compression of a breast (depicted by dotted line 354). Since the rigid substrate 304 is manufactured of a transparent plastic, the breast 354 may still be viewed therethrough, and adequately positioned, prior to further compression. Further, by having portions of the breast 354 visible, automatic exposure control (AEC) procedures may also be performed. The AEC may be totally automatic, where the system searches the breast or portion thereof, following a pre-pulse exposure, for the densest region to determine optimal exposure. A plurality of AEC markers are depicted on the compression paddle 300. These markers are can be used in lieu of the automatic AEC algorithm, and if selected, identify for the algorithm the region of the breast upon which to base the exposure. A number of the AEC markers are present proximate removable portions 302a of the foam compressive material 302. As such, prior to compression, an appropriate AEC marker may be selected based on a position of the breast, presence of the foam, or other factors, for proper dose measurement and recordation.

During use, a technologist may first remove one or more of the removable portions 302a of the foam compressive material 302. The portions of the foam compressive material 302 remaining in place, in that case, would be secured to the rigid substrate 304 as described elsewhere herein, e.g., by an adhesive. Once the breast 354 is placed in its initial position, it may be minimally compressed by the foam compressive material 302 proximate the leading edge surface 310 so as to generally stabilize its position. Once the initial compression is performed, the technologist may reinsert the removed portion(s) 302a of the foam compressive material into their original position, adjacent the foam compressive material 302. This may be performed by manipulating or compressing by hand the removed portions 302a and fitting them into the proper position. Once so positioned, compression may continue until the imaging condition described above is reached. Although compression to the imaging condition may be obtained without reinsertion of the subsidiary portions 302a, reinsertion thereof helps ensure an even application of force across the breast 354, and eliminates the potential for bulges, tissue folds, and the like, which can have an adverse effect on the resultant images. It has been discovered, however, that the edges of the foam compressive material 302 proximate subsidiary portions 302a may form image artifacts, even when the subsidiary portions 302a are in place for imaging. These artifacts may be removed during post-imaging processing.

Figure 3B:
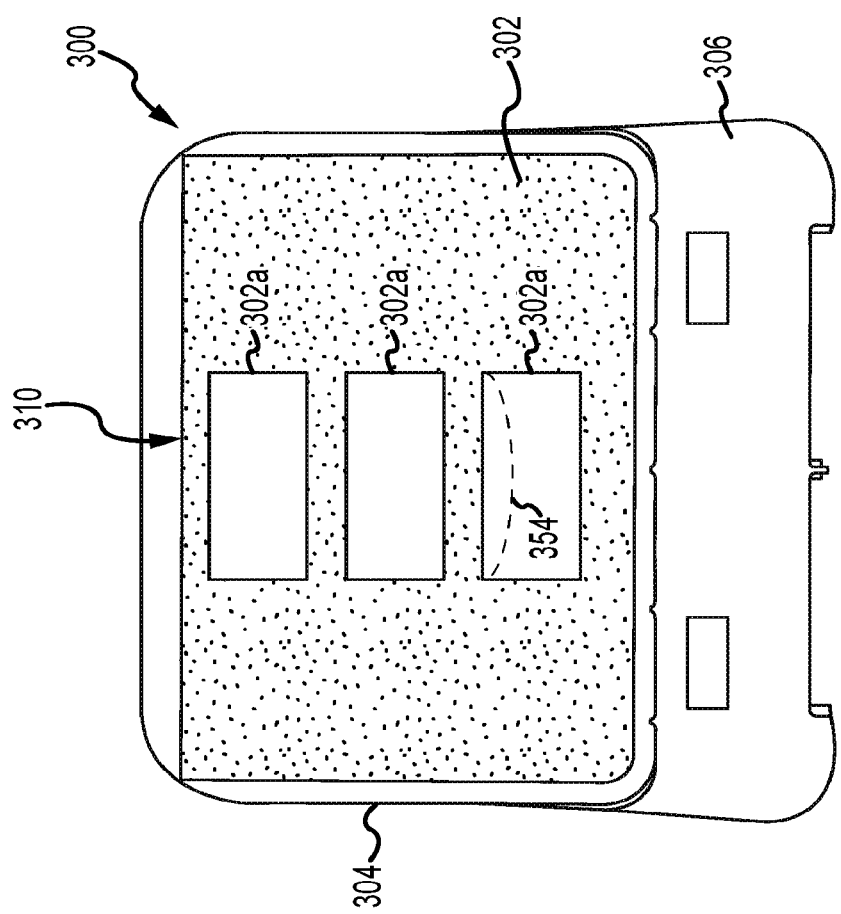
FIG. 3B is a top view of a compression paddle having a plurality of removable portions of a foam compressive element in accordance with another example.

FIG. 3B is a top view of a compression paddle 300 having a plurality of removable portions of a foam compressive element 302 in accordance with another example. As described above with regard to FIG. 3A, the compression paddle 300 includes subsidiary portions 302a that may be removed prior to significant compression of a breast 354, so the breast 354 may remain visible, to ease positioning thereof. Once the breast 354 is placed in its initial position, it may be minimally compressed by the foam compressive material 302 proximate the leading edge surface 310 so as to generally stabilize its position. Once the initial compression is performed, the technologist may reinsert the subsidiary portion(s) 302a of the foam compressive material into their original position, in this case surrounded by the foam compressive material 302. Other removable portions may be differently shaped. For example, triangles, ovals, or cut-outs of other shapes may be utilized and positioned anywhere on the compression paddle 300, as required or desired for a particular application.

Figure 4:
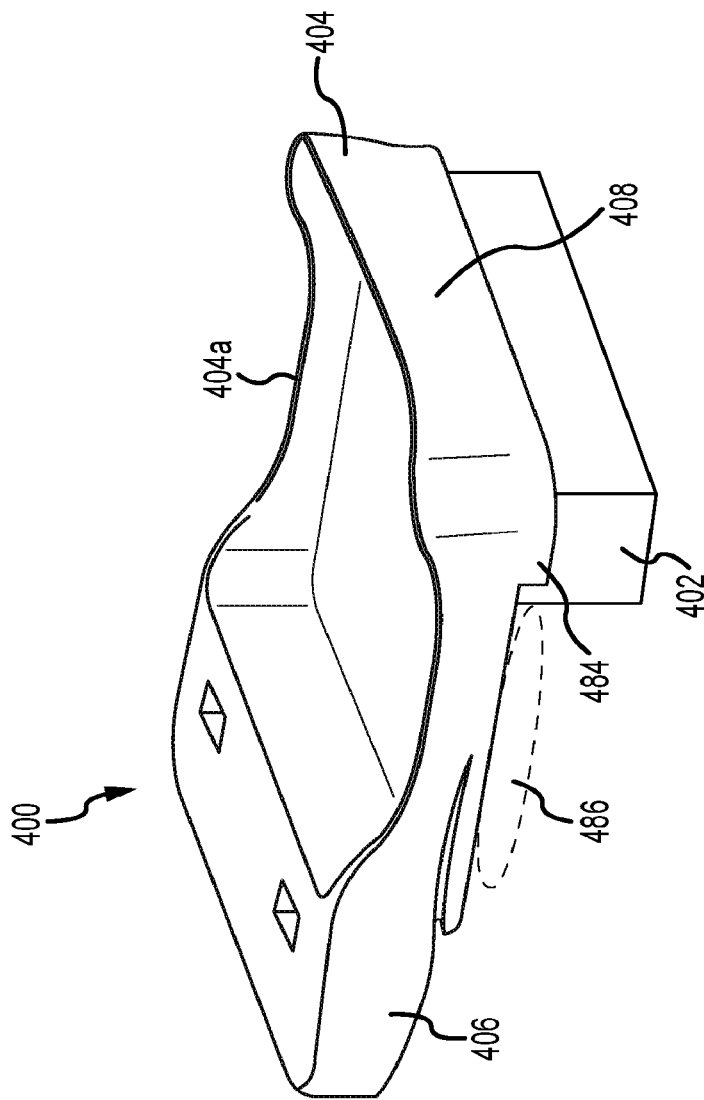
FIG. 4 is a perspective view of a compression paddle having a foam compressive element in accordance with another example.

FIG. 4 is a perspective view of a compression paddle 400 having a foam compressive element 402 in accordance with another example. The paddle 400 includes a bracket portion 406, generally integral with the substrate 404 for connecting the paddle 400 to compression arm of an imaging system. The paddle 400 also includes a leading face 408, opposite the bracket portion 406, which is disposed proximate a chest wall of a patient during compression and imaging procedures. A projecting portion 484 of the substrate 404 proximate the leading face 408 extends downward towards the breast (not shown). A foam compressive material 402, such as described elsewhere herein, is secured to a bottom (and optionally, sides) of the projecting portion 484. Raised walls 404a provide additional rigidity.

The paddle 400 depicted in FIG. 4 is particularly useful in MLO-view mammograms and tomosynthesis procedures in the MLO position. In such a position, it is desirable that the axilla be able to be visualized and, as such, a biologically-meaningful amount of foam 402 must extend from the chest wall. The actual thickness of foam utilized may be varied based on the size of the breast. It has been determined, for example, that approximately two inches of foam 402 would be desirable for the largest breasts. Smaller breasts may not require a foam 402 of such thickness. Restricting the foam 402 to only a biologically meaningful area maximizes the visibility of the breast by the technologist, who is able to visualize the remainder of the breast through the portions of the substrate 404 that do not have foam disposed thereunder. Additionally, positioning the projecting portion 484 and foam 402 as depicted in FIG. 4, allows for stabilization of the breast wall and pectoral muscle. Thus the breast is readily stabilized and discomfort reduced.

Further, only a portion of the paddle (e.g., the foam 402) is intended to touch the breast. By disposing the foam material 402 below the projecting portion 484, a small volume 486 is formed. Thus, the natural elastic deformation of the breast will minimize the chance of skin folds appearing while maximizing ease of access to the breast for the technologist. The gap 486, in one example, may be about 19 mm high (e.g., similar to the thickness of an average hand) for ease of access. In another example, the gap 486 may be about five mm high to restrict the maximum amount of maximum breast thickness variation to under one cm. Further, the configuration limits or prevents potential sagging. Further, when used during tomosynthesis, the necessity of complete compression to separate tissues for improved visualization is reduced, thus making the configuration depicted in FIG. 4 viable for greater comfort. In standard mammogram imaging, the maximum variability in breast thickness is also minimized with the depicted paddle 400.

Figure 5:
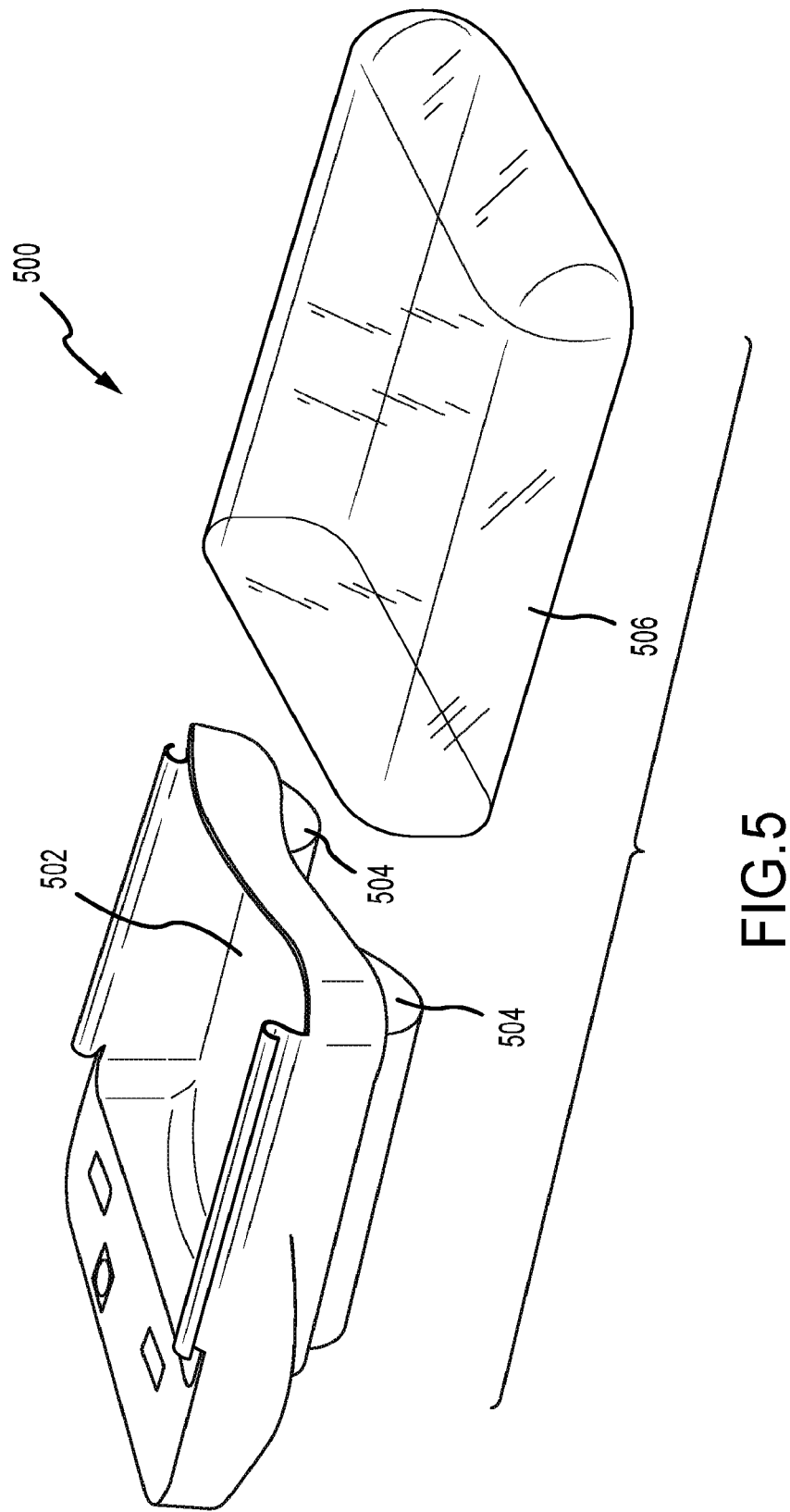
FIG. 5 depicts an exploded perspective view of a multi-material breast compression paddle.

FIG. 5 depicts an exploded perspective view of a multi-material breast compression paddle 500. This paddle 500 includes a rigid plastic portion or body 502, one or more thick foam profiles 504, and a thin flexible material 506b that substantially surrounds the rigid plastic body 502 and the foam profiles 504. The foam profiles 504 are positioned so as to improve visibility of the breast, e.g., since they are generally located proximate side walls 512 of the paddle 500. Details of the rigid body 502 are described below. With regard to the thin material 506, it may be manufactured in the form of a sheath or bag that may substantially surround the compression paddle 500. In this configuration, the entire compression paddle 500, including the base 502 and the foam profiles 504 are covered by the thin material 506. This helps prevent contamination of the body 502 and foam profiles 504 by bodily fluids, such as sweat or blood (which may be produced during biopsy procedures). The depicted thin material 506 may also be a shrink-wrap material as described above. After an application of heat to the shrink-wrap material 506 (once disposed over the paddle 500), the shrink-wrap material 506 is difficult to remove from the compression paddle 500 without permanent damage or deformation (e.g., cutting, slicing, or tearing). It may be desirable that the foam profiles 504 provide a resistance to deformation that is greater than the corresponding force applied by the shrink-wrap material 506. This would help prevent significant deformation of the foam profiles 504 due to shrinking of thin material 506, prior to further deformation of the foam profiles 504 due to breast compression.

In examples where the thin material 506 is a shrink-wrap material or other similar tight-fitting material, the thin material 506 may be applied to the compression element 500 prior to conducting a breast imaging procedure. Heat is then applied to the compression element 500 and the thin material 506 to cause the thin material 506 to shrink and increase the tension of the portion of the flexible material 506 spanning the foam profiles 504, but without applying such tension as to substantially compress the profiles 504. In some examples, the heating process may occur at a time just prior to the breast imaging procedure in order to warm the breast compression element 500 to increase patient comfort as the breast is compressed. Additionally, the thin material 506 is advantageously disposable. As such, after use with a first patient, the thin material 506 may be removed and a new thin material 506 may be applied for a subsequent patient. This may eliminate the need to clean or otherwise treat the surface of the breast compression element 500 between patients.

Figure 6A:
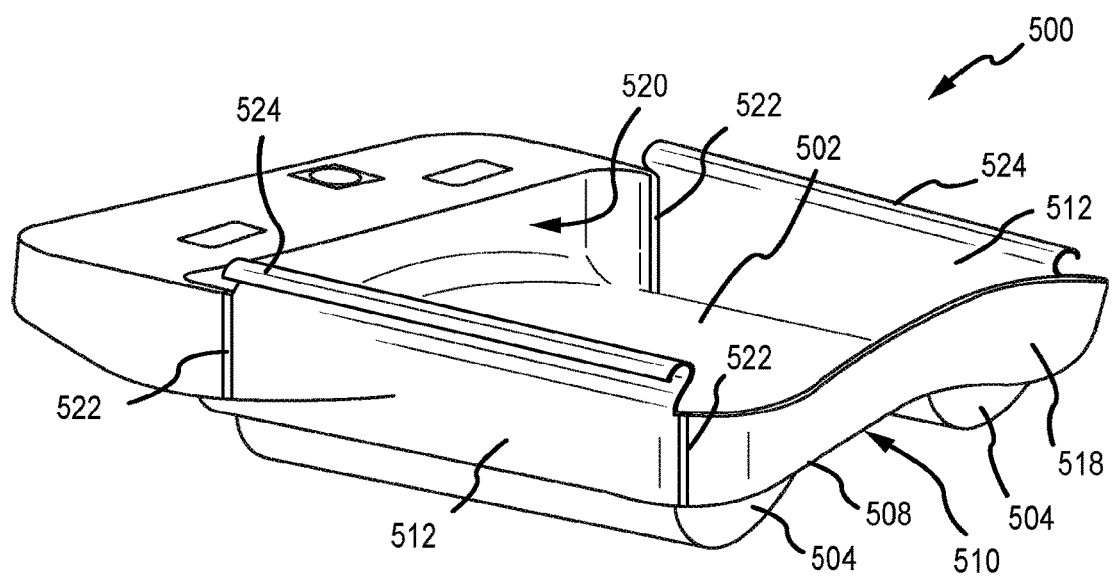
FIGS. 6A-6C depict partial perspective, front, and side views, respectively, of an example of the breast compression paddle of FIG. 5.
Figure 6B:
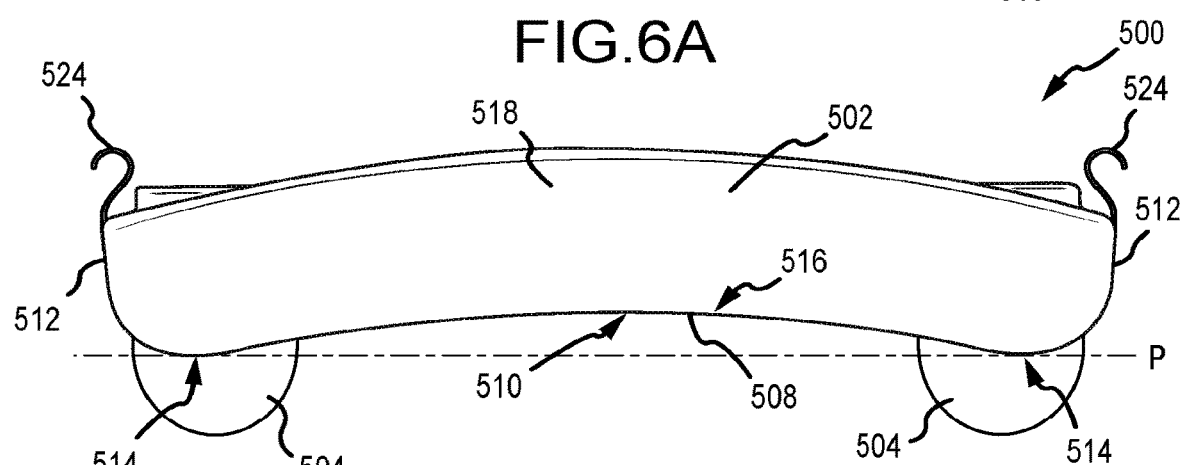
Figure 6C:
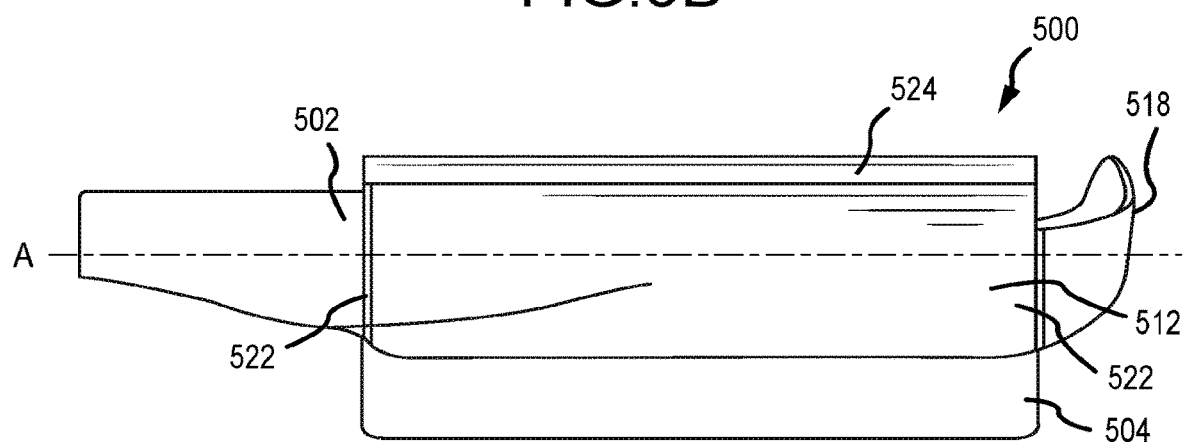

FIGS. 6A-6C depict partial perspective, front, and side views, respectively, of an example of the breast compression paddle 500 of FIG. 5. The thin material is not depicted for clarity. Performance of the compression paddle 500 with the thin material in place is described below with regard to FIGS. 7A and 7B. As described above, the compression paddle 500 includes the body 502 and the foam profiles 504. The body 502 is generally formed of a single piece of rigid plastic. A bottom wall or base 508 of the compression paddle 500 includes a generally concave surface 510, which generally may correspond in shape to a breast and/or a compressed breast. The generally concave surface 510 extends generally between the side walls 512 of the compression paddle 500. The generally concave surface 510 helps to distribute more equally forces applied to the breast to more closely correspond to the shape of the breast. Such a configuration may help provide more comfort to a patient as the breast is being compressed. Additionally, the generally concave surface 510 provides a volume into which the thin material may deflect during a compression of the breast, as described in more detail below. The generally concave surface 510 includes two outer edge portions 514 that define a reference plane P. A central portion 516 is non-coplanar with the outer edge portions 514, such that the central portion 516 is raised relative to or disposed above the reference plane P. The central portion 516 may be level (e.g., parallel to the reference plane P or an axis A of the paddle 500) or may be pitched downward from a front wall 518 to a rear wall 520 of the paddle 500. This may help further conform the paddle 500 to the shape of the breast.

Adjacent walls of the paddle 500 (e.g., the side walls 512, the front wall 518, and rear wall 520) may be separated from each other by a gap or slot 522 that extends from an upper edge of each wall to a location proximate the base 508. These gaps or slots 522 allow for greater flexure of the various walls (e.g., the side walls 512 for reasons described below). Flexure of the front wall 518 may also improve patient comfort as that feature contacts the chest wall during a compression procedure. Each of the side walls 512 may include a structure or wall extension 524 extending upwards therefrom, which acts as a tensioning element for the thin flexible material so as to maintain tension thereon during breast compression. The structures 524 may be integral with the side walls 512 or discrete therefrom. The shape of the structures 524 may vary depending on the application, although the curled structure depicted in the figures may be advantageous to prevent damage to the thin material. Further, the structure 524 may extend to a height at or just above the tallest component of the compression paddle 500 (in this case, the front wall 518). This allows the structure 524 to maintain tension on the thin material, even as the structure 524 deflects.

The thin material is also used to provide a cover to the one or more foam profiles 504, so as to prevent contamination by bodily fluids so the foam profiles 504 may be reused with a number of patients. Two foam profiles 504 are depicted in FIG. 5 as substantially semi-cylindrical elements secured to the base 508 of the compression paddle 500, generally near the side walls 512 of the paddle 500. By locating the foam profiles 504 near the side walls 512 (which are the lowest portion of the generally concave surface 510), the raised central portion 516 of the paddle 500 remains above an uppermost portion of the foam profile 504. The foam profiles 504 may be secured with adhesive to the base 508. The foam profiles 504 increase separation between the thin material and the base 508 of the compression paddle 500, so as to enable the performance described below. The curved bottom surfaces of the foam profiles 504 allow the thin material to be wrapped smoothly therearound so as to maintain tension thereof.

Figure 7A:
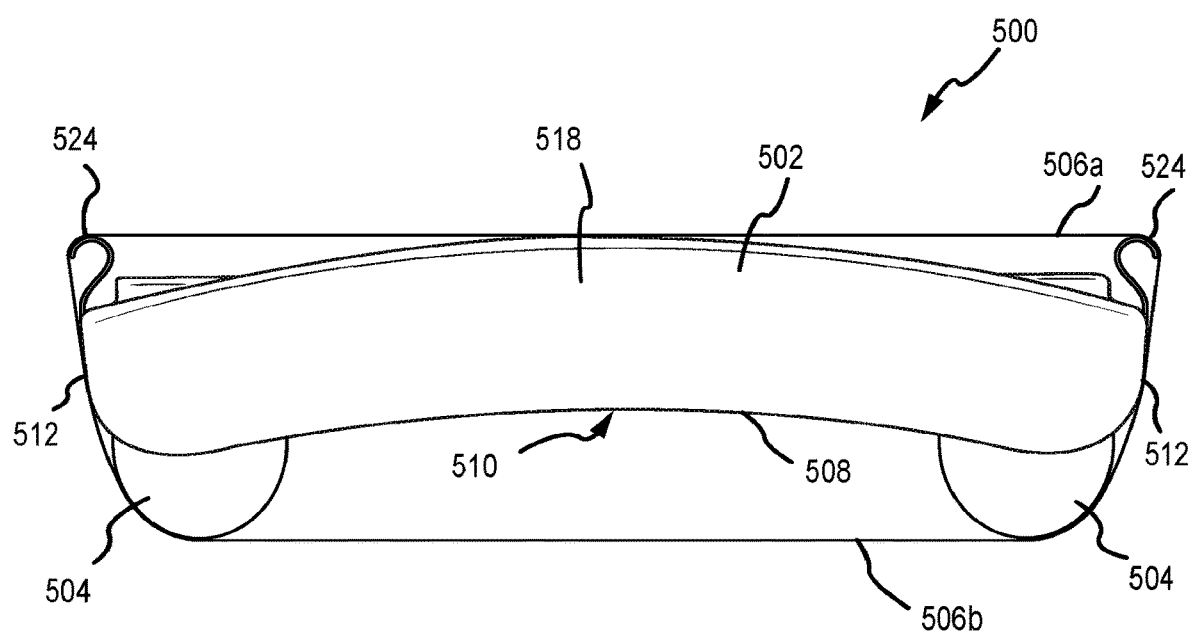
FIGS. 7A and 7B depict a front view of the breast compression paddle of FIG. 5 in a first and a second position.
Figure 7B:
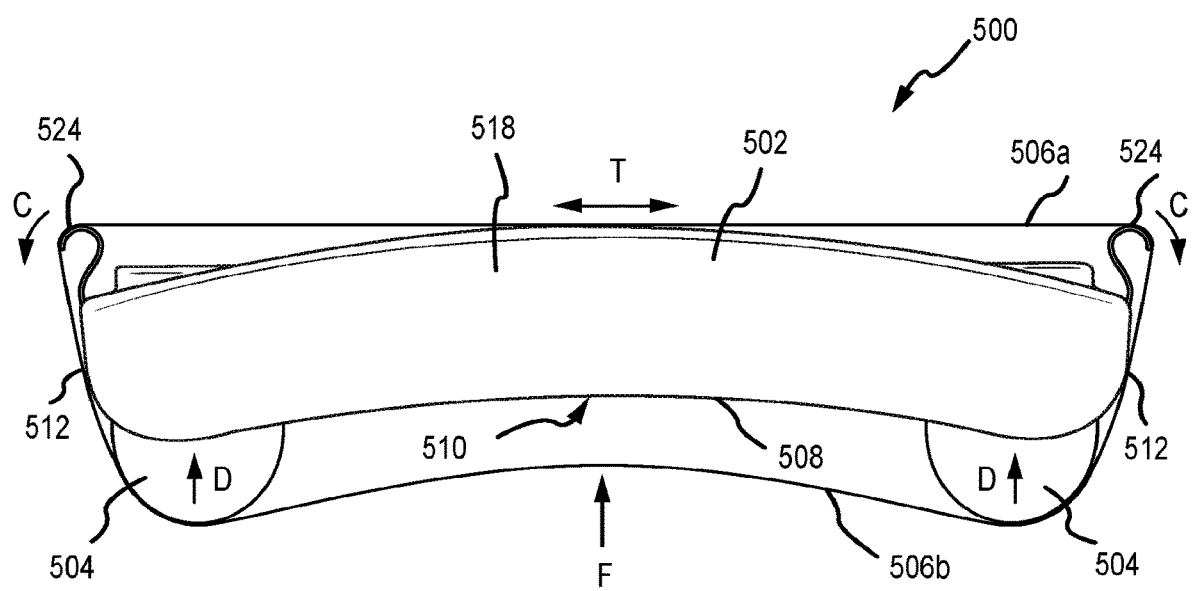

FIGS. 7A and 7B depict a front view of the breast compression paddle 500 of FIG. 5 in a first and a second condition, respectively. The first condition of FIG. 7A is when the breast compression paddle 500 is in a neutral condition (e.g., when the paddle 500 is not compressing a breast). In this condition, the thin material 506 remains relatively taut around the paddle 500. Depending on the paddle 500 configuration, the thin material 506 may contact a portion of the side walls 512, as it does here. Further, the thin material 506 may be in contact with the front wall 518, if the thin material 506 is in a bag-shaped configuration. Further, the thin material 506 wraps around the foam profiles 504 and, depending on the force applied thereto, may compress slightly those profiles 504, even in this neutral position. Tension on the thin material 506 is generally maintained by the structures 524 on each side wall 512.

In the second condition of FIG. 7B, a force F is applied to an underside 506b of the thin material 506. This may occur when the paddle 500 is pressed against a breast, for example, to compress or otherwise stabilize the breast for an imaging procedure. As the applied force F deflects the underside 506a upward, the foam profiles 504 are configured to deflect D. The amount of deflection D may be based at least in part on the density of the foam profile 504 material, amount of force F applied, elasticity of the thin material 506, resiliency of the tensioning structures 524, and other factors. Further, as the force F increases, the tensioning structures 524 may deflect in a curve C or other direction downward such that tension T on the topside 506a of the thin material 506 increases. This helps maintain tension on the thin material 506 so that material does not collapse due to force F. Thus, when the compression paddle 500 is used to compress a breast, the foam profiles 504 and thin material 506 act to stabilize the breast as compression begins. Compression may continue, however, until the foam profiles 504 deform completely, and force is applied directly to the breast via the base 508 (with the thin material 506 located therebetween). The configuration of the foam profiles 504 as depicted in FIGS. 7A and 7B are particularly advantageous for compression performed in the MLO position. The foam profiles 504 provide increased comfort to the patient, specifically because they are disposed such that the upper of the two profiles 504 contacts the axilla tissue proximate the armpit. As such, compression of that location is cushioned by the foam profile 504.

FIG. 8 is a top view of a compression paddle 600 having a foam compressive element 602 in accordance with another example. The foam compressive material 602 is secured to the rigid substrate 604, as described elsewhere herein. In this example, the foam compressive material 602 includes a curved outer contour 602a that mimics the shape of a breast. This curved outer contour 602a need not be a consistent curve along the entire length thereof. Regardless, this curved outer contour 602a may define the outer and inner lateral edge surfaces 614, 616. At least one advantage associated with such a curved outer contour 602a includes increased visibility of the breast for positioning. Additionally, since breast imaging systems can be visibly intimidating to a patient (and associated with discomfort), the curved outer contour 602a may give the impression of a more pleasant experience.

Figure 9A:
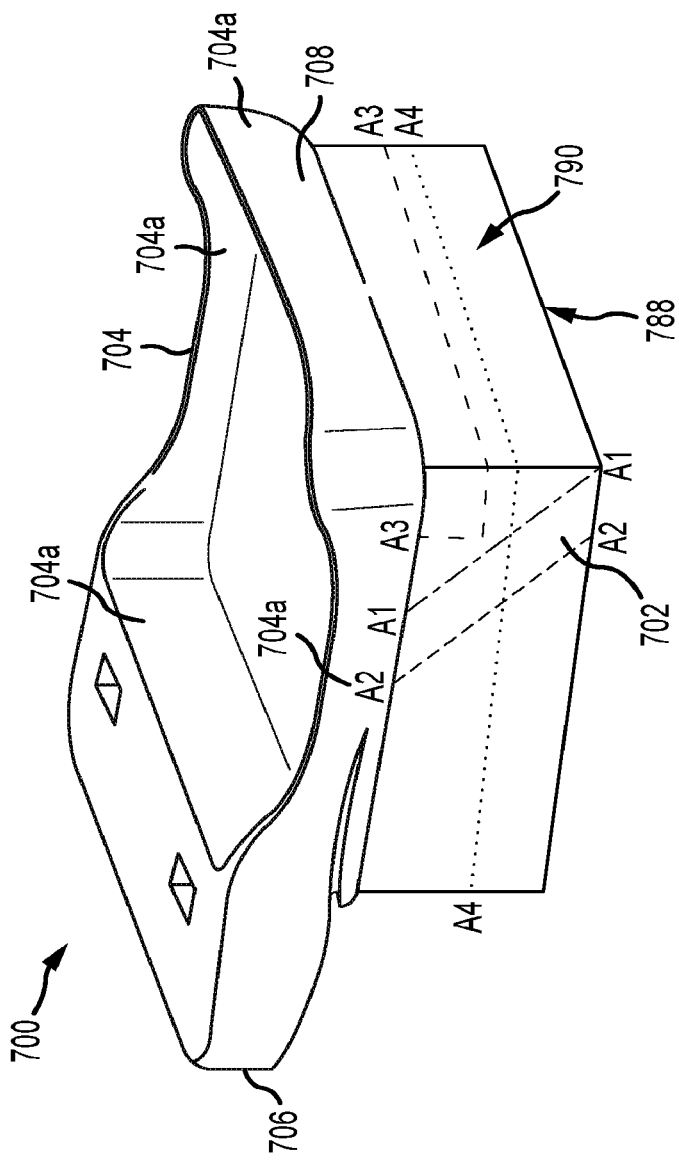
FIG. 9A is a perspective view of a compression paddle having a foam compressive element in accordance with another example.

FIG. 9A is a perspective view of a compression paddle 700 having a foam compressive element 702 in accordance with another example. As with the above paddles, the paddle 700 includes a bracket portion 706, generally integral with the substrate 704 for connecting the paddle 700 to compression arm of an imaging system. The paddle 700 also includes a leading face 708, opposite the bracket portion 706, which is disposed proximate a chest wall of a patient during compression and imaging procedures. Raised walls 704a provide additional rigidity. The foam compressive element 702 includes a compression surface 788 that is both substantially parallel to a bottom surface of the substrate 704 and is configured to contact a breast during compression (although a biocompatible cover may be disposed between the foam compressive element 702 and the breast, as described above).

The compressive element 702 in FIG. 9A utilizes multiple pieces of foam, each having different densities. The configuration and orientation of the two pieces of foam allows for different regions of the foam compressive element 702 to resist compression differently, leading to greater comfort, more even compression, and other benefits. A number of different configurations are depicted in FIG. 9A with various dashed lines. In general, a first foam having a first density is depicted on one side of a line, while a second foam having a second density on the other side of the line. The various lines represent discrete abutments between adjacent pieces of foam, typically where an adhesive may be located to secure the foam pieces together. In another example, a first portion of the foam may be formed, then placed in a mold where a second portion of the form may be formed thereon, thus obviating the need for an adhesive. Typically only one abutment is utilized in a compressive element 702 (e.g., joining two discrete foam portions of two different densities). In other examples, however, multiple abutments may be utilized to join more than two discrete foam portions to each other. In such a case, adjacent foam portions may have different densities, but non-adjacent foam portions may have the same densities. In other examples, the foam compressive element 702 may be of single-piece construction having varying densities throughout.

Abutment A1 is disposed at a non-perpendicular angle to a leading edge surface 790 and the compression surface 788 and intersects the interface between those two surfaces 788, 790. The angle of abutment A1 relative to the compression surface 788 may vary as required or desired for a particular application. In this example, the location of abutment A1 results in only a single one of the foam portions (here, the portion to the left of abutment A1) to form the compression surface 788. Abutment A2 is disposed at a non-perpendicular to the leading edge surface 790 and the compression surface 788, but intersects directly and only the compression surface 788. As such, both foam portions disposed on either side of abutment A2 form the compression surface 788. Paddles 700 having compressive element 702 configured consistent with abutments A1 or A2 may include a foam portion of a higher density disposed to the right of each respective abutment. These higher density foams compress less than the lower density foams disposed to the left of the abutment, which may help pull breast tissue away from the chest wall for imaging, while reducing discomfort for the patient.

Abutment A3 is disposed at a perpendicular or substantially perpendicular angle to both the leading edge surface 790 and the compression surface 788, but intersects only the leading edge surface 790. In this example, the location of abutment A3 results in only a single one of the foam portions (here, the portion to the left of and below abutment A3) to form the compression surface 788. If a higher density foam is used in the portion of the compressive element 702 above and to the right of abutment A3, this configuration of a compressive element 702 may help pull breast tissue away from the chest wall.

Abutment A4 is disposed substantially perpendicular to the leading edge surface 790 and substantially parallel to the compression surface 788; thus, only the foam portion below abutment A4 forms the compressive surface 788. If a lower density foam is disposed below the abutment A4, that portion of the compressive element 702 will provide greater cushioning for a breast at lower compression forces. As the compression forces increase, greater compression will occur due to the location of the foam portion above the abutment A4.

Abutments A1-A4 depicted in FIG. 9A and described above are for illustrative purposes only. Compressive elements 702 having other configurations of abutments are contemplated. Such other configurations may include multiple abutments, such that more than two foam portions may be utilized in a single compressive element. Further, non-planar abutments may be utilized as required or desired; wave-like, curved, and concave or convex abutments are contemplated. The abutments described herein essentially separate the compressive element 702 into multiple volumes of discrete compressive forces, thus greatly customizing the functionality of each compressive element 702 to compress the breast in ways advantageous to improve imaging, comfort, or even compression. Other advantages would be apparent to a person of skill in the art.

Figure 9B:
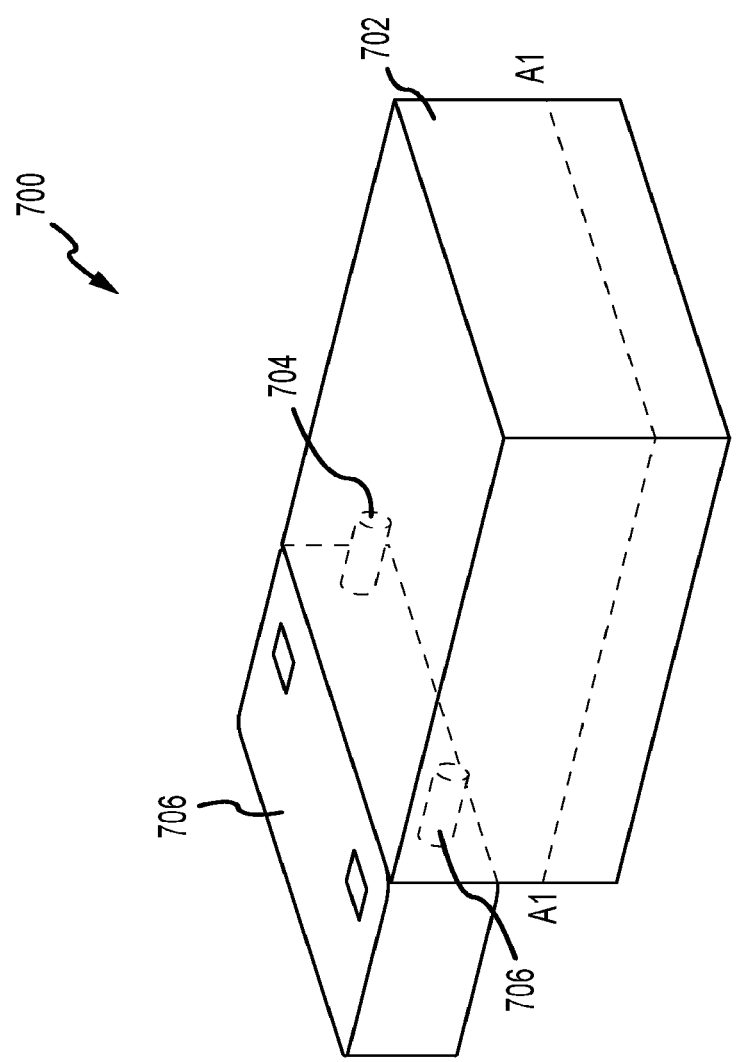
FIG. 9B is a perspective view of a compression paddle having a foam compressive element in accordance with another example.

FIG. 9B is a perspective view of a compression paddle 700 having a foam compressive element 702 in accordance with another example. As with the above paddles, the paddle 700 includes a bracket portion 706. The foam compressive element 702 may be directly secured to the bracket 706 or may be formed around or otherwise secured to an underlying structure or skeleton 704, which may provide some structural rigidity without the need for a complete substrate as described above. In this example a single abutment A1 is depicted between two foams having different densities (e.g., a higher density foam above the abutment A1, with a lower density foam below). Other orientations of abutments, such as described above, are contemplated.

Figure 10:
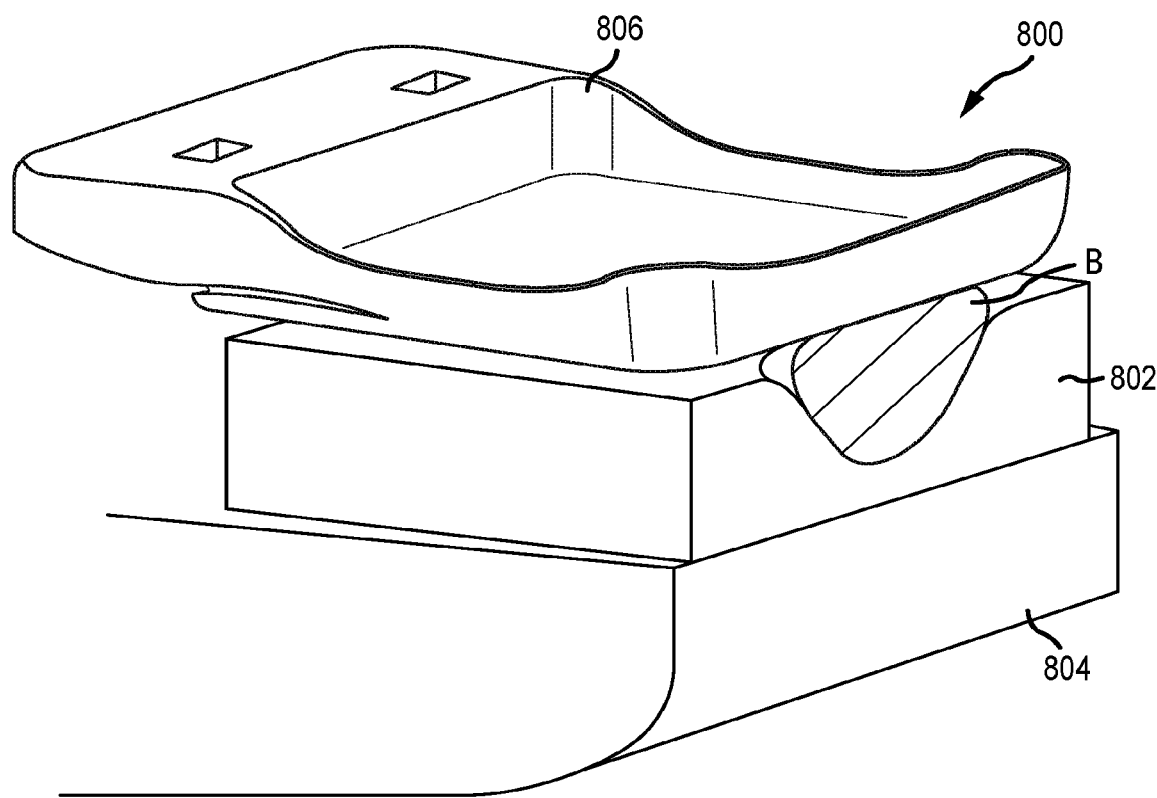
FIG. 10 is a partial perspective view of an imaging system including a thick foam compressive element disposed on a support platform thereof.

FIG. 10 is a partial perspective view of an imaging system 800 including a thick foam compressive element 802 disposed on a support platform 804 thereof. A breast B is compressed between the foam compressive element 802 and a compression paddle 806. By disposing the foam compressive element 802 below the breast B, a number of advantages (in addition to the general aspects of improved comfort) are attained. For example, comfort is further improved since the foam compressive element 802 provides an insulating effect from the typically cold support platform 804. Friction between the breast B and the foam compressive element 802 helps in positioning of the breast B, especially in the MLO imaging position. The breast B remains more visible to the technician, unlike configurations where a foam compressive element is positioned above a breast. Further, disposing a foam compressive element having about a 2 inch thickness below the breast results in only a 4% increase in dose at the Automatic Exposure Control breast thickness, when measured via automatic exposure control.

Figure 11A:
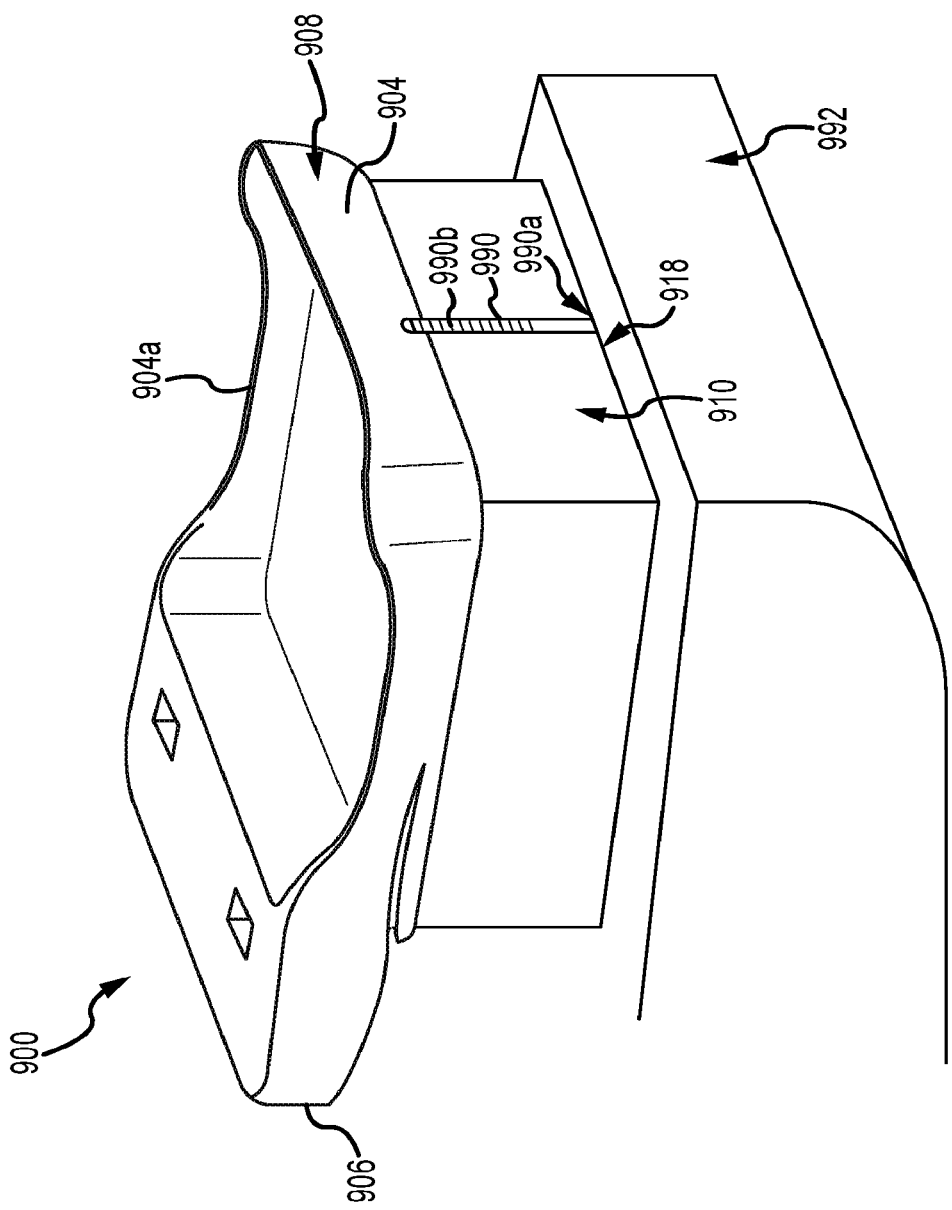
FIG. 11A is a perspective view of a compression paddle having a foam compressive element and a compression detector in a first position.
Figure 11B:
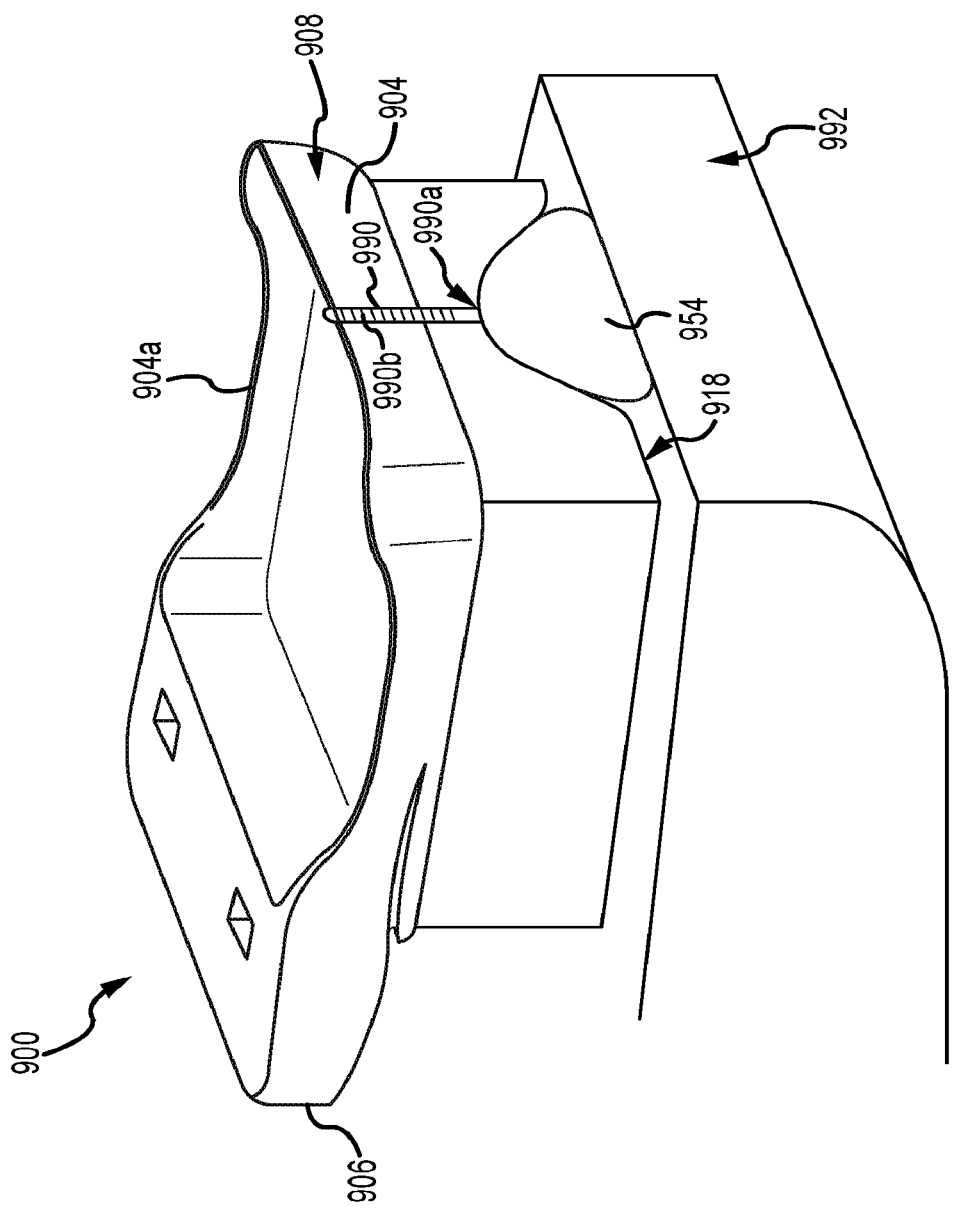
FIG. 11B is a perspective view of the compression paddle of FIG. 5A having the foam compressive element and the compression detector in a second position.

FIGS. 11A and 11B are front views of a compression paddle 900 having a foam compressive element 902 and a compression detector 990 in a first position and a second position, respectively. As described elsewhere herein, the compression paddle 900 includes a rigid substrate 904 having raised walls 904a, and a bracket 906. A breast support platform 992 is also depicted. Disposed proximate the leading edge surface 910 is a compression detector 990, which is used to determine the amount of compression of the foam compressive material 902 proximate the leading edge surface 910, where the most compression typically occurs. In examples, the compression detector 990 is a rigid radiolucent material, such as a fiber optic pin, which may be secured to a leading face 908 of the rigid substrate 904. The compression detector 990 may be secured with brackets (not shown) against which the pin 990 may slide. In another example, the compression detector 990 may be embedded in the foam compressive material 902. Regardless of the configuration, a bottom 990a of the pin 990 is generally coextensive with the compressive surface 918. Thus, as a breast 954 is compressed between the foam compressive material 902 and the breast platform 992, the foam compressive material 902 compresses and the pin 990 moves upward a distance generally corresponding to the amount of compression of the foam compressive material 902. Gradation marks 990b on the pin 990 may be read manually by a technologist or automatically by an optical or other reader (not shown) associated with the paddle 900 and/or the imaging system. By reading the gradation marks, the total amount of compression of the foam compressive material 902 may be determined and analyzed relative to the force applied, calculated height of the breast 954, etc. This may be particularly useful for AEC exposure techniques. The gradation marks 990b, representing a thickness of the foam compressive material 902, may be used as an offset to approximate a thickness of the breast 954. The gradation marks 990b may be read automatically by a sensor or visualized and entered by the technologist into an associated AEC program. The thickness may be subtracted automatically from a measurement corresponding to a distance of the compression paddle 900 above the support platform 992 so as to determine a thickness of the breast 954. This thickness may then be used to determine the appropriate AEC exposure control technique.

Figure 12:
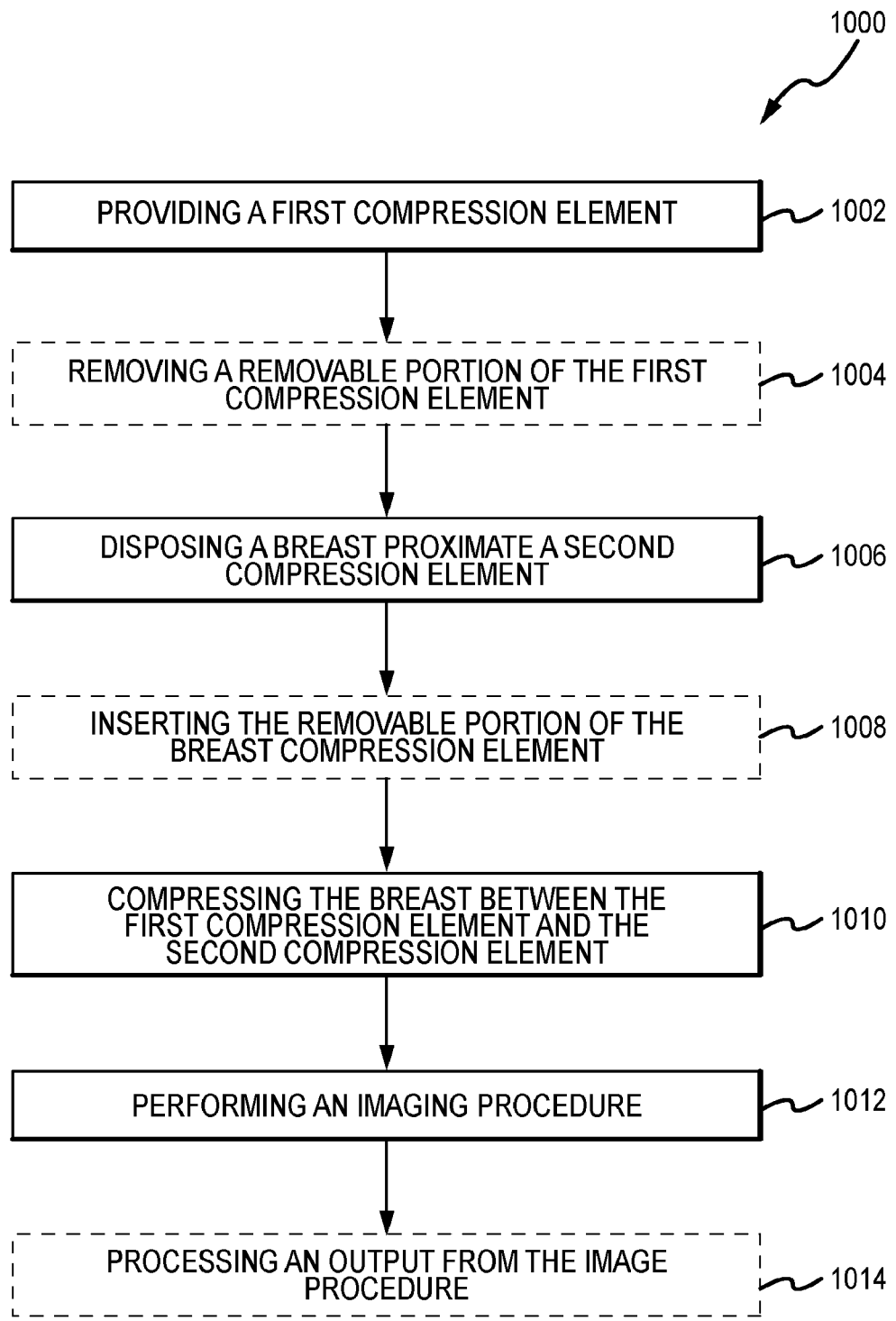
FIG. 12 depicts a method of compressing a breast in an imaging system.

FIG. 12 depicts a method 1000 of compressing a breast in an imaging system. The method 1000 begins with providing a first compression element, operation 1002. The first compression element may be a compression paddle including a rigid substrate and a foam secured to the rigid substrate, such as described herein. The foam may include an inner lateral edge surface, an outer lateral edge surface, a mid-plane disposed between the inner lateral edge surface and the outer lateral edge surface, a leading edge surface, a compressive surface, and an interface connecting the leading edge surface and the compressive surface. Optional operation 1004 includes removing one or more removable portions of the foam. Compression elements having removable portions of foam are described herein. This operation may be performed prior to or after operation 1006, which includes disposing the breast on a second compression element. The second compression element may be a breast support platform disposed facing the compressive surface. During placement of the breast, a chest wall of the patient is substantially aligned with the leading edge surface, and an inner side of the breast is disposed proximate the inner lateral edge surface and an outer side of the breast is disposed proximate the outer lateral edge surface. If optional operation 1004 was performed, operational operation 1008, inserting the removable portion(s) of the foam prior to compressing the breast, may also be performed.

In operation 1010 compressing the breast between the first compression element and the second compression element is performed. The breast is compressed to an imaging condition, wherein in the imaging condition, a portion of the leading surface aligned with the mid-plane is compressed to an incompletely compressed condition. When in the imaging condition, the interface may define a first curve adjacent an outer side of the mid-plane and a second curve adjacent an inner side of mid-plane, while a straight portion of the interface is substantially parallel to the second compression element. An imaging procedure, such as a tomosynthesis imaging procedure, is performed in operation 1012. Subsequent thereto, optional operation 1014 may be performed, which includes processing an output from the imaging procedure so as to adjust a visibility of an artifact formed by the removable portion. The processing may include processing of the images as known in the art to obtain the set of tomosynthesis slice images. Processing may also include removing artifacts appearing in the images.

FIGS. 11A and 11B, above, describe use of a compression detector 590 to determine foam thickness and thus breast thickness. In other examples, automatic exposure control (AEC) software may be utilized with the foam compression systems described herein to determine breast thickness, without requiring the compression detector 590. A portion of the AEC system identifies the thickness of the compressed breast, which will differ from the compression paddle height above the support platform due to the thickness of the foam. Image processing software, which identifies and corrects the breast shape to provide a mammogram-like image, may also be utilized in imaging systems employing foam compressive elements. Because the shape of the breast compressed by foam will differ from the flat shape of a breast compressed using a rigid flat paddle, this image correction may prove beneficial. Breast thickness may also be determined from the acquired tomosynthesis images. This information may be stored, along with information obtained from the images, such as breast density, and may be used to calculate the delivered breast dose. The AEC is utilized to control the exposure so as to deliver a required dose to the detector. Following this exposure, the AEC calculates the actual delivered breast dose based on breast thickness and exposure information such as kV and mAs. This information may be saved for later access and use.

Figure 13:
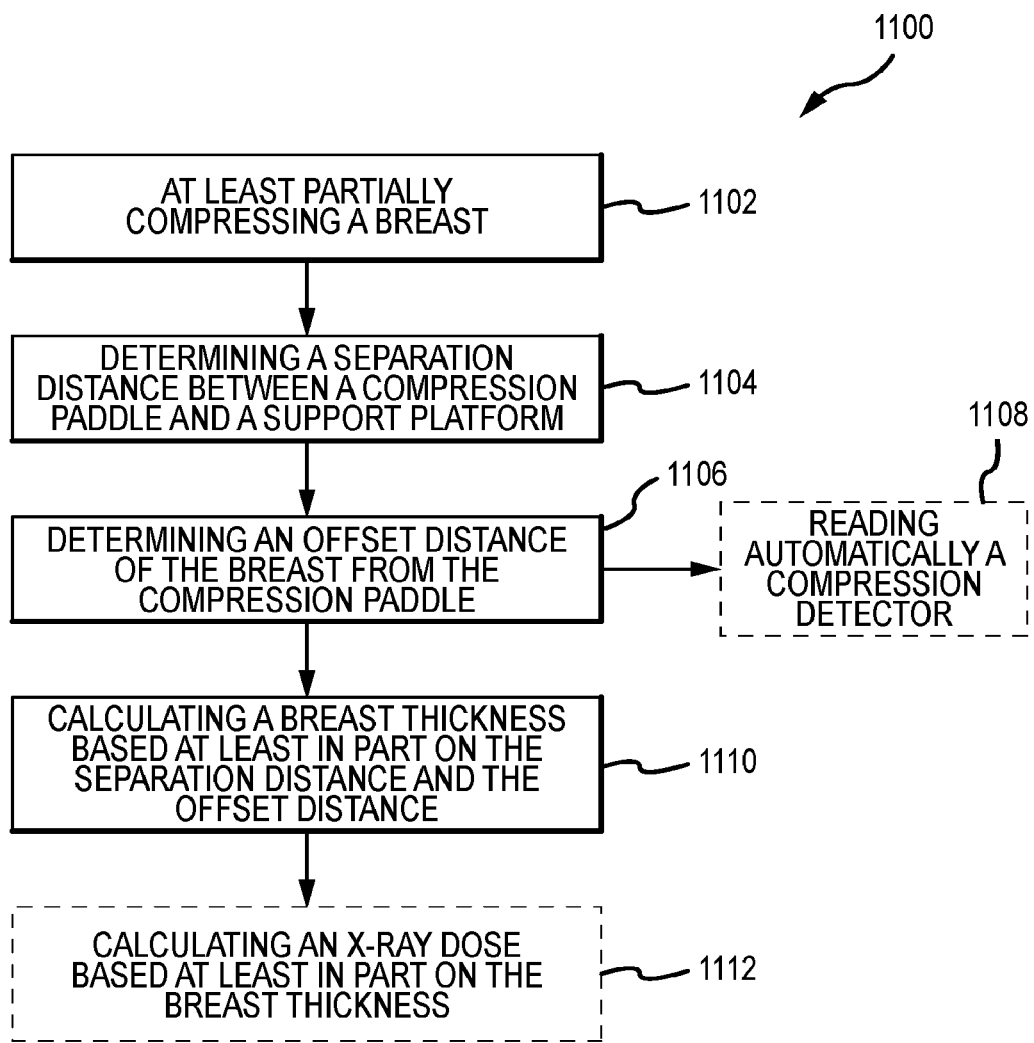
FIG. 13 depicts a method of calculating a thickness of a compressed breast.

FIG. 13 depicts one method 1100 of calculating a thickness of a compressed breast. The method begins with operation 1102, at least partially compressing a breast between a support platform and a compression paddle. The compression paddle may include a compressive foam material in contact with the breast, such as the examples depicted herein. In operation 1104, a separation distance between the compression paddle and the support platform is determined. In examples, the separation may be determined utilizing encoders associated with the compression systems of a breast imaging device, by using linear or other encoder, proximity sensors, or other position sensors. In operation 1106, an offset distance of the breast from the compression paddle is determined. This offset distance corresponds to a compressed thickness of the compressive foam material. In examples, determining the offset includes reading automatically a compression detector, operation 1108, such as the compression detector described in conjunction with FIGS. 11A and 11B. In operation 1110, a breast thickness based at least in part on the separation distance and the offset distance is determined. This information may be utilized to perform further imaging of a breast, for example, to calculate an x-ray exposure technique based at least in part on the breast thickness, operation 1112. Mammography image quality and patient radiation dose depend on the x-ray exposure techniques, such as choice of anode material, x-ray energy (kVp), and x-ray filter material. An accurately or reasonably calculated or estimated breast thickness helps ensure the proper x-ray exposure technique to be used for the breast under compression.

Figure 14:
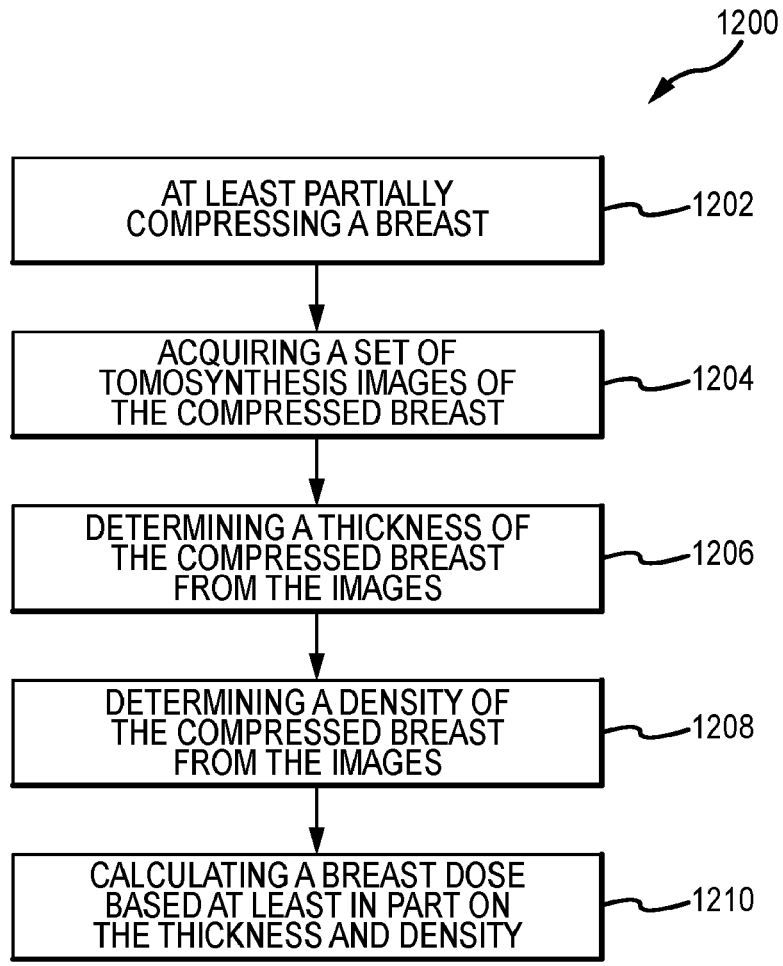
FIG. 14 depicts a method of determining an imaging dose for a compressed breast.

FIG. 14 depicts a method 1200 of determining a radiation dose for a compressed breast. The method begins with operation 1202, at least partially compressing a breast between a support platform and a compression paddle. The compression paddle may include a compressive foam material in contact with the breast, such as the examples depicted herein. Operation 1204 includes acquiring a set of tomosynthesis images of the compressed breast. From these tomosynthesis images, a number of characteristics of the breast may be determined. For example, operation 1206 contemplates determining a thickness of the compressed breast based at least in part on the tomosynthesis images. Operation 1208 contemplates determining a density of the compressed breast based at least in part on the tomosynthesis images. From this information, a breast dose for x-ray imaging may be calculated based at least in part on the determined thickness and density. Due to uncertainties present when mechanically measuring the actual breast thickness under a compression paddle with foam material, this imaging-based method may provide more accurate breast thickness and density data, resulting in more accurate estimate of breast radiation dose from the exam.

Figure 15:
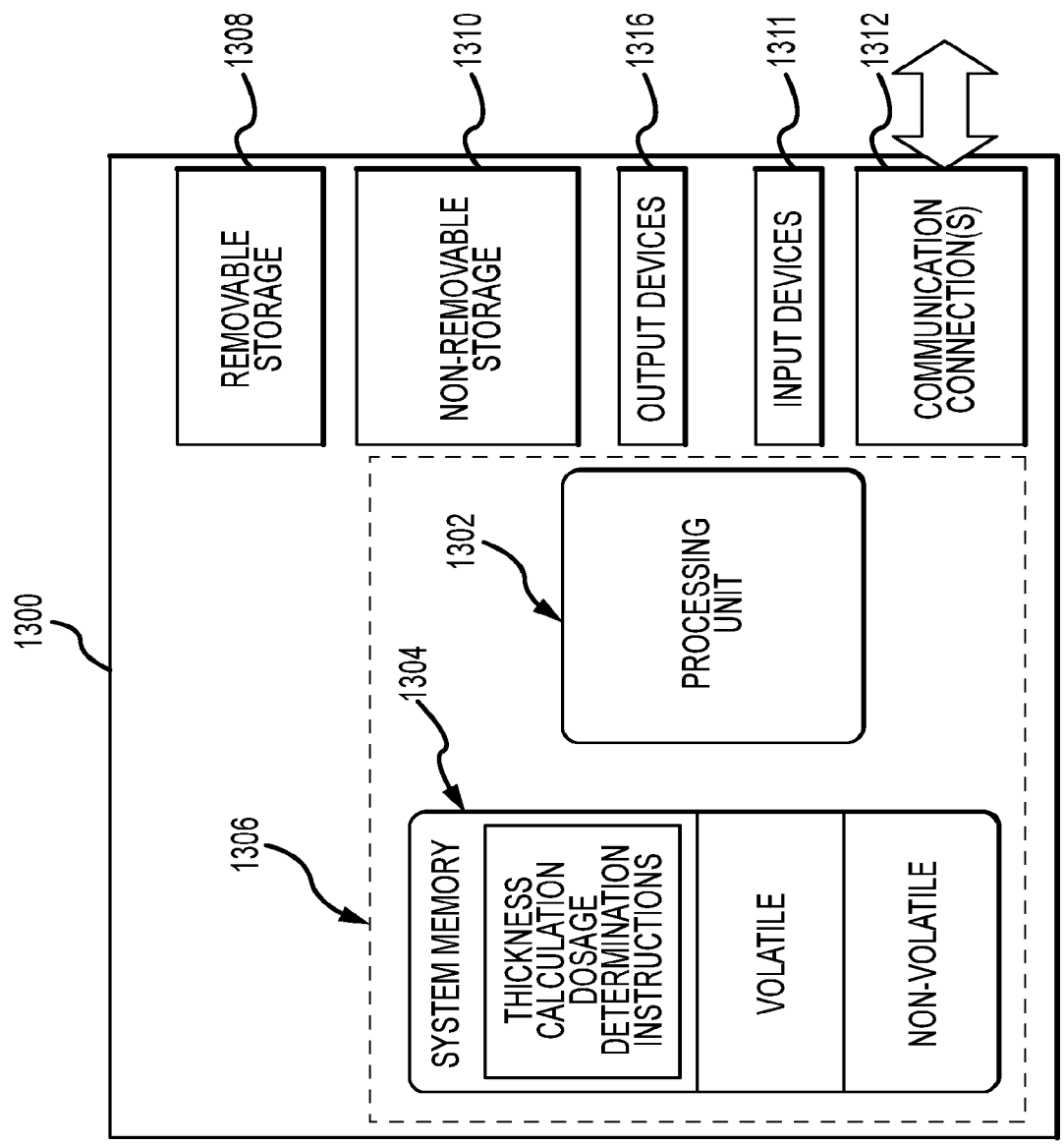
FIG. 15 depicts an example of a suitable operating environment in which one or more of the present examples can be implemented.

FIG. 15 illustrates one example of a suitable operating environment 1300 in which one or more of the present examples can be implemented. This operating environment may be incorporated directly into the imaging systems disclosed herein, or may be incorporated into a computer system discrete from, but used to control, a the imaging and compression systems described herein. This is only one example of a suitable operating environment and is not intended to suggest any limitation as to the scope of use or functionality. Other well-known computing systems, environments, and/or configurations that can be suitable for use include, but are not limited to, imaging systems, personal computers, server computers, hand-held or laptop devices, multiprocessor systems, microprocessor-based systems, programmable consumer electronics such as smart phones, network PCs, minicomputers, mainframe computers, tablets, distributed computing environments that include any of the above systems or devices, and the like.

In its most basic configuration, operating environment 1300 typically includes at least one processing unit 1302 and memory 1304. Depending on the exact configuration and type of computing device, memory 1304 (storing, among other things, instructions to calculate breast thickness, determine x-ray dosages, or perform other methods disclosed herein) can be volatile (such as RAM), non-volatile (such as ROM, flash memory, etc.), or some combination of the two. This most basic configuration is illustrated in FIG. 11 by dashed line 1306. Further, environment 1300 can also include storage devices (removable, 1308, and/or non-removable, 1310) including, but not limited to, magnetic or optical disks or tape. Similarly, environment 1300 can also have input device(s) 1314 such as touch screens, keyboard, mouse, pen, voice input, etc., and/or output device(s) 1316 such as a display, speakers, printer, etc. Also included in the environment can be one or more communication connections 1312, such as LAN, WAN, point to point, Bluetooth, RF, etc.

Operating environment 1300 typically includes at least some form of computer readable media. Computer readable media can be any available media that can be accessed by processing unit 1302 or other devices having the operating environment. By way of example, and not limitation, computer readable media can include computer storage media and communication media. Computer storage media includes volatile and nonvolatile, removable and non-removable media implemented in any method or technology for storage of information such as computer readable instructions, data structures, program modules or other data. Computer storage media includes, RAM, ROM, EEPROM, flash memory or other memory technology, CD-ROM, digital versatile disks (DVD) or other optical storage, magnetic cassettes, magnetic tape, magnetic disk storage or other magnetic storage devices, solid state storage, or any other tangible medium which can be used to store the desired information. Communication media embodies computer readable instructions, data structures, program modules, or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer readable media. A computer-readable device is a hardware device incorporating computer storage media.

The operating environment 1300 can be a single computer operating in a networked environment using logical connections to one or more remote computers. The remote computer can be a personal computer, a server, a router, a network PC, a peer device or other common network node, and typically includes many or all of the elements described above as well as others not so mentioned. The logical connections can include any method supported by available communications media. Such networking environments are commonplace in offices, enterprise-wide computer networks, intranets and the Internet.

In some embodiments, the components described herein include such modules or instructions executable by computer system 1300 that can be stored on computer storage medium and other tangible mediums and transmitted in communication media. Computer storage media includes volatile and non-volatile, removable and non-removable media implemented in any method or technology for storage of information such as computer readable instructions, data structures, program modules, or other data. Combinations of any of the above should also be included within the scope of readable media. In some embodiments, computer system 1300 is part of a network that stores data in remote storage media for use by the computer system 1300.

Figure 16:
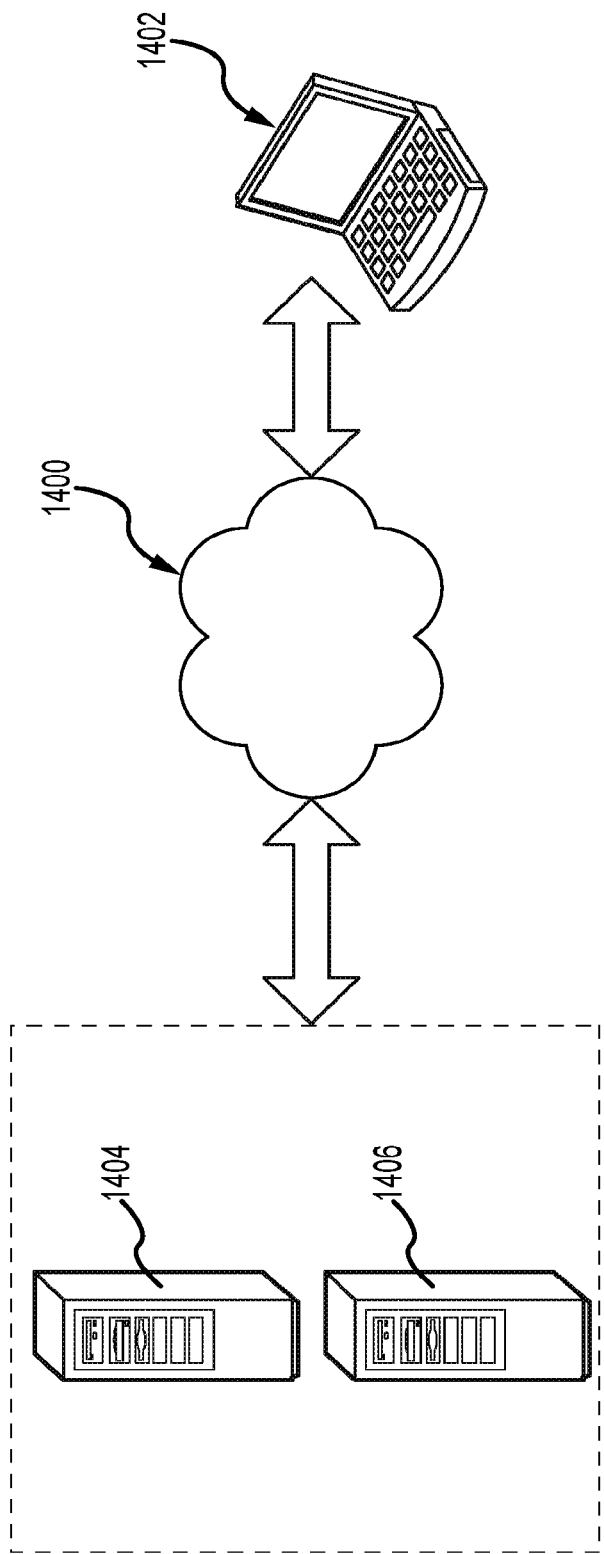
FIG. 16 depicts an example of a network in which the various systems and methods disclosed herein may operate.

FIG. 16 is an embodiment of a network 1400 in which the various systems and methods disclosed herein may operate. In embodiments, a client device, such as client device 1402, may communicate with one or more servers, such as servers 1404 and 1406, via a network 1408. In embodiments, a client device may be a standalone imaging system (e.g., imaging system 120 depicted in FIG. 1A) that includes all the functionality described herein. The client device may also include or incorporate a laptop, a personal computer, a smart phone, a PDA, a netbook, or any other type of computing device, such as the computing device in FIG. 15. In examples, such a client device may be connected to an imaging system. In embodiments, servers 1404 and 1406 may also be any type of computing device, such as the computing device illustrated in FIG. 15. Network 1408 may be any type of network capable of facilitating communications between the client device and one or more servers 1404 and 1406. For example, the surface image data and the internal image data may be acquired locally via the imaging systems and communicated to another computing device(s) for further processing, such as an image acquisition workstation or a cloud-based service. Examples of such networks include, but are not limited to, LANs, WANs, cellular networks, and/or the Internet.

In embodiments, the various systems and methods disclosed herein may be performed by one or more server devices. For example, in one embodiment, a single server, such as server 1404 may be employed to perform the systems and methods disclosed herein, such as the methods for imaging discussed herein. Client device 1402 may interact with server 1404 via network 1408. In further embodiments, the client device 1402 may also perform functionality disclosed herein, such as scanning and image processing, which can then be provided to servers 1404 and/or 1406.

This disclosure described some examples of the present technology with reference to the accompanying drawings, in which only some of the possible examples were shown. Other aspects can, however, be embodied in many different forms and should not be construed as limited to the examples set forth herein. Rather, these examples were provided so that this disclosure was thorough and complete and fully conveyed the scope of the possible examples to those skilled in the art.

Although specific examples were described herein, the scope of the technology is not limited to those specific examples. One skilled in the art will recognize other examples or improvements that are within the scope of the present technology. Therefore, the specific structure, acts, or media are disclosed only as illustrative examples. Examples according to the technology may also combine elements or components of those that are disclosed in general but not expressly exemplified in combination, unless otherwise stated herein. The scope of the technology is defined by the following claims and any equivalents therein.

What is claimed is:

1. An imaging system comprising:
   an x-ray source;
   an immobilization assembly having a breast support platform and a moveable paddle configured to immobilize a patient's breast for x-ray imaging, the immobilization assembly including a foam compressive element;
   an x-ray detector disposed within the breast support platform; and
   a compression detector configured to determine compression of at least a portion of the foam compressive element.

2. The imaging system of claim 1, wherein the foam compressive element includes a leading edge surface configured to face a chest wall of a patient during immobilization of the patient's breast, the compression detector disposed proximate the leading edge surface so as to measure compression of the foam compressive element proximate the leading edge surface.

3. The imaging system of claim 1, wherein the compression detector includes a rigid radiolucent material.

4. The imaging system of claim 3, wherein the rigid radiolucent material is a fiber optic pin.

5. The imaging system of claim 4, wherein a bottom of the pin is generally coextensive with a compressive surface of the foam compressive element.

6. The imaging system of claim 4, wherein the fiber optic pin includes gradation marks.

7. The imaging system of claim 6, wherein the gradation marks represent a thickness of the foam compressive element.

8. The imaging system of claim 1, wherein the compression detector is at least partially embedded in the foam compressive element.

9. The imaging system of claim 1, wherein the foam compressive element is coupled to the breast support platform.

10. The imaging system of claim 1, wherein the foam compressive element is coupled to the paddle.

11. The imaging system of claim 1, wherein the foam compressive element includes a compressive surface, at least a portion of the compression detector movable with the compressive surface.

12. An imaging system comprising:
    an x-ray source;
    an immobilization assembly having a breast support platform and a moveable paddle configured to immobilize a patient's breast for x-ray imaging, the immobilization assembly including a foam compressive element coupled to the breast support platform, the foam compressive element having a leading edge surface configured to face a chest wall of a patient;
    an x-ray detector disposed within the breast support platform; and
    a compression detector configured to determine compression of at least a portion of the foam compressive element proximate the leading edge surface and relative to the breast support platform.

13. The imaging system of claim 12, wherein the compression detector includes a pin having gradation marks, the gradation marks representing a thickness of the foam compressive element.

14. The imaging system of claim 13, wherein the foam compressive element includes a compressive surface and a bottom of the pin is generally coextensive with the compressive surface.

15. The imaging system of claim 13, wherein the x-ray source has an x-ray exposure technique, the x-ray exposure technique is based at least partially on a compression thickness of the foam compressive element determined by the compression detector.

16. The imaging system of claim 12, wherein the compression detector is embedded in the foam compressive element.

17. The imaging system of claim 12, wherein the foam compressive element is secured to the breast support platform.

18. A method of immobilizing a patient's breast on an imaging system having an x-ray source and an x-ray detector, the method comprising:
    immobilizing the patient's breast in an immobilization assembly of the imaging system, the immobilization assembly having a breast support platform and a moveable paddle, the immobilization assembly including a foam compressive element;
    determining a separation distance between a surface of the paddle and a surface of the breast support platform, the patient's breast disposed between the two surfaces;
    determining, by a compression detector, a compressed thickness of the foam compressive element; and
    calculating a breast thickness based at least in part on the separation distance and the compressed thickness.

19. The method of claim 18, wherein the compression detector includes a pin with gradation marks, and the method further comprises sensing a position of the pin with a sensor or visualizing a position of the pin by a technologist.

20. The method of claim 18, further comprising calculating an x-ray exposure technique based at least on part on the breast thickness.

* * * * *